(12) United States Patent
Wang et al.

(10) Patent No.: US 9,656,992 B2
(45) Date of Patent: May 23, 2017

(54) PYRIMIDINE COMPOUNDS FOR THE TREATMENT OF HEPATITIS C

(71) Applicant: BRISTOL-MYERS SQUIBB COMPANY, Princeton, NJ (US)

(72) Inventors: Tao Wang, Farmington, CT (US); Christopher Allard, Amston, CT (US); Paul Michael Scola, Glastonbury, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/771,914

(22) PCT Filed: Mar. 5, 2014

(86) PCT No.: PCT/US2014/020661
§ 371 (c)(1),
(2) Date: Sep. 1, 2015

(87) PCT Pub. No.: WO2014/138199
PCT Pub. Date: Sep. 12, 2014

(65) Prior Publication Data
US 2016/0159769 A1    Jun. 9, 2016

Related U.S. Application Data

(60) Provisional application No. 61/773,980, filed on Mar. 7, 2013.

(51) Int. Cl.
A61K 45/06    (2006.01)
A61K 31/506    (2006.01)
C07D 401/12    (2006.01)
C07D 401/14    (2006.01)
C07D 417/14    (2006.01)
C07D 413/14    (2006.01)
A61K 31/5377    (2006.01)

(52) U.S. Cl.
CPC .......... *C07D 401/12* (2013.01); *A61K 31/506* (2013.01); *A61K 31/5377* (2013.01); *A61K 45/06* (2013.01); *C07D 401/14* (2013.01); *C07D 413/14* (2013.01); *C07D 417/14* (2013.01)

(58) Field of Classification Search
CPC .... A61K 45/06; A61K 31/506; C07D 401/12; C07D 401/14; C07D 417/14; C07D 413/14
See application file for complete search history.

(56) References Cited

U.S. PATENT DOCUMENTS 8,765,944 B2    7/2014    Sun et al.

FOREIGN PATENT DOCUMENTS

WO    01/47897    *    7/2001
WO    WO 01/47897 A1    7/2001

* cited by examiner

*Primary Examiner* — Alexander R Pagano
*Assistant Examiner* — Ebenezer O Sackey
(74) *Attorney, Agent, or Firm* — James Epperson

(57) ABSTRACT

The disclosure provides compounds of formula I, including pharmaceutically acceptable salts, as well as compositions and methods of using the compounds. The compounds have activity against hepatitis C virus (HCV) and may be useful in treating those infected with HCV.

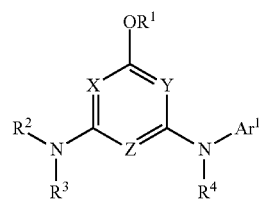

(I)

13 Claims, No Drawings

PYRIMIDINE COMPOUNDS FOR THE TREATMENT OF HEPATITIS C

CROSS-REFERENCE TO RELATED APPLICATIONS

This application claims priority to U.S. Provisional Patent Application Ser. No. 61/773,980, filed Mar. 7, 2013, which is incorporated by reference in its entirety.

BACKGROUND OF THE INVENTION

The disclosure generally relates to the novel compounds of formula I including pharmaceutically acceptable salts, which have activity against hepatitis C virus (HCV) and are useful in treating those infected with HCV. The disclosure also relates to compositions and methods of using these compounds.

Hepatitis C virus (HCV) chronically infects an estimated 170 million people worldwide, with 3 to 4 million infected individuals in the United States alone (Boyer, N. and Marcellin, P. *J. Hepatology.* 2000, 32:98-112; Alter, M. J., et al. *Engl. J. Med.* 1999, 341:556-562). Prior to the mid 1990s, transfusion with infected blood products was the main route of HCV transmission. Following the introduction of blood screening methods, transmission via injection drug use became the primary risk factor. Chronic infection often leads to the development of severe liver complications, including fibrosis, cirrhosis, and hepatocellular carcinoma. HCV infection is also the leading cause of orthotopic liver transplantation in the United States. The degree to which disease progression is related to viral and cellular factors is not completely understood.

Considerable heterogeneity is found within the nucleotide and encoded amino acid sequence of the HCV genome (Simmonds, P. *J. Gen. Virology.* 2004, 85:3173-3188). Based on this sequence diversity, six major genotypes and multiple associated subtypes have been described. The genotypes of HCV differ in their worldwide distribution, and the clinical significance of the genetic heterogeneity of HCV remains elusive despite numerous studies of the possible effect of genotypes on pathogenesis and therapy.

Medical treatment for HCV is limited by the lack of a vaccine or approved therapies that specifically target the virus. Currently, patients undergo treatment with a combination of parenterally administered pegylated alpha-interferon and oral ribavirin. Genotype 1 HCV is the most difficult to treat and elimination of the virus (sustained virologic response) is achieved for only approximately 50% of patients (Fried, M. W. et al. *N. Engl. J. Med.* 2002, 347:975-982; Zeumzem, S. *Nature Clinical Practice.* 2008, 5:610-622). This poor treatment response, combined with often severe side effects induced by therapy, highlight a need for improved antiviral drugs with better efficacy and safety profiles.

HCV is a member of the Flaviviridae family of viruses with a single-stranded positive-sense RNA genome. Following infection of host cells, the 9.6 Kb genome is translated into a polyprotein precursor of approximately 3,000 amino acids (reviewed in Lindenbach, B. D. and Rice, C. M. *Nature.* 2005, 436:933-938; Moradpour, D, Penin, F., and Rice, C. M. *Nature Reviews.* 2007, 5:453-463). Post-translational processing by both cellular and viral proteases results in the generation of at least 10 separate viral proteins. The structural proteins (which by definition are found in mature virions) include core, E1, E2, and possibly p7, and originate from the amino-terminal region of the polyprotein. The core protein assembles into the viral nucleocapsid. The E1 and E2 glycoproteins form heterodimers that are found within the lipid envelope surrounding the viral particles, and mediate host cell receptor binding and entry of the virus into cells. It is unclear if p7 is a structural protein, and its role in replication has yet to be defined. However p7 is believed to form an ion channel in cellular membranes, preventing acidification of intracellular compartments in which virions are assembled, and it has been shown to be essential for viral replication and assembly. The nonstructural proteins NS2, NS3, NS4A, NS4B, NS5A, and NS5B are produced through maturational cleavages of the carboxy-terminal region of the polyprotein. NS2 along with the amino terminus of NS3 form the NS2-3 metalloprotease which cleaves at the NS2-NS3 junction. Additionally, NS2 is involved in assembly and egress of nascent virions. The NS3 protein contains both a serine protease in its amino-terminal region, and a nucleotide-dependent RNA helicase in its carboxy-terminal region. NS3 forms a heterodimer with the NS4A protein, constituting the active protease which mediates cleavages of the polyprotein downstream of NS3, both in cis, at the NS3-NS4A cleavage site, and in trans, for the remaining NS4A-NS4B, NS4B-NS5A, NS5A-NS5B sites. The complex formation of the NS3 protein with NS4A seems necessary to the processing events, enhancing the proteolytic efficiency at all of the sites. The NS3 protein also exhibits nucleoside triphosphatase and RNA helicase activities. The NS4B protein has been shown to be important for localization of HCV proteins into replication complexes in altered membranous structures within the cell. NS5B encodes an RNA-dependent RNA polymerase that is involved in the replication of HCV.

Subgenomic HCV replicons, containing the untranslated regions 5' and 3' to the coding sequence fused to the nonstructural proteins or the full-length polyprotein, are competent for translation, viral protein expression, and replication within cultured cells (Lohmann, V. et al. *Science.* 1999, 285:110-113; Moradpour, D, Penin, F., and Rice, C. M. *Nature Reviews.* 2007, 5:453-463). The replicon system has proven valuable for the identification of inhibitors targeting the nonstructural proteins associated with these functions. However, only limited subsets of HCV genotypes have been used to generate functional replicons.

Other systems have been used to study the biology of the HCV structural proteins that mediate the entry into host cells. For example, virus-like-particles made in recombinant baculovirus-infected cells with the HCV core, E1 and E2 proteins have also been used to study the function of the HCV E1 and E2 proteins (Barth, H., et al. *J. Biol. Chem.* 2003, 278:41003-41012). In addition, pseudotyping systems where the E1 and E2 glycoproteins are used to functionally replace the glycoproteins of retroviruses have been developed (Bartosch, B., Dubuisson, J. and Cosset, F.-L. *J. Exp. Med.* 2003, 197:633-642; Hsu, M. et al. *Proc. Natl. Acad. Sci. USA.* 2003, 100:7271-7276). These systems yield HCV pseudoparticles that bind to and enter host cells in a manner which is believed to be analogous to the natural virus, thus making them a convenient tool to study the viral entry steps as well as to identify inhibitors block this process.

Recently, a full-length genotype 2a HCV clone, JFH1, was isolated and demonstrated the ability to replicate in vitro. Through repeated passage and adaptation in cell culture increased titers of infectious virus were produced (Lindenbach, B. D., et al. *Science.* 2005, 309:623-626; Wakita, T. et al. *Nature Med.* 2005, 11:791-796). In contrast to the HCV replicon or pseudotyping systems, the infectious virus is useful for studying the complete HCV replication cycle, including identifying inhibitors of not only the replication proteins, but those involved in early steps in virus infection (entry and uncoating) and production of progeny viruses (genome packaging, nucleocapsid assembly, virion envelopment and egress).

Triazines have been disclosed. See WO 2009/091388 and US 2009/0286778.

The invention provides technical advantages, for example, the compounds are novel and are effective against hepatitis C. Additionally, the compounds provide advantages for pharmaceutical uses, for example, with regard to one or more of their mechanism of action, binding, inhibition efficacy, target selectivity, solubility, safety profiles, or bioavailability.

DESCRIPTION OF THE INVENTION

One aspect of the invention is a compound of formula I

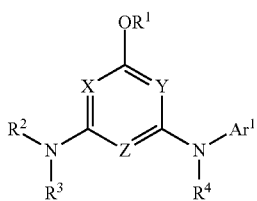

where
X and Y are N and Z is CH; Y and Z are N and X is CH; or X and Z are N and Y is CH;
$R^1$ is alkyl, hydroxyalkyl, alkoxyalkyl, haloalkyl, cycloalkyl, hydroxycycloalkyl, alkoxycycloalkyl, halocycloalkyl, cycloalkenyl, indanyl, alkylcarbonyl, or benzyl wherein the benzyl moiety is substituted with 0-3 substituents selected from halo, alkyl, haloalkyl, alkoxy, and haloalkoxy;
$R^2$ is alkyl, $(Ar^2)$alkyl, $(Ar^2)$cycloalkyl, $((Ar^2)$cycloalkyl)alkyl, $((Ar^2)$alkyl)cycloalkyl, or $(((Ar^2)$alkyl)cycloalkyl)alkyl;
$R^3$ is hydrogen or alkyl;
$R^4$ is hydrogen or alkyl;
$R^5$ is

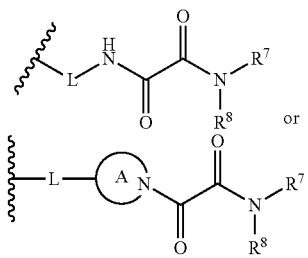

where ring A is a 4 to 7 membered alkylene ring substituted with L;
$R^6$ is hydrogen or alkyl;
$R^7$ is hydrogen, alkyl, cycloalkyl, (cycloalkyl)alkyl, (alkyl) cycloalkyl, ((alkyl))cycloalkyl)alkyl, a bridged bicycloalkyl, or $Ar^3$, and is substituted with 0-4 substituents selected from the group consisting of halo, alkyl, cycloalkyl, hydroxyalkyl, alkoxyalkyl, hydroxy, alkoxy, benzyloxy, $CO_2R^9$, $N(R^{10})(R^{11})$, tetrahydrofuranyl, tetrahydropyranyl, and $Ar^4$;
$R^8$ is hydrogen or alkyl;
or $R^7$ and $R^8$ taken together with the nitrogen to which they are attached is azetidinyl, pyrrolidinyl, piperidinyl, piperazinyl, morpholinyl, or tetrahydroisoquinolinyl, and is substituted with 0-2 substituents selected from alkyl, alkylcarbonyl, and alkoxycarbonyl;
$R^9$ is hydrogen, alkyl, hydroxyalkyl, alkoxyalkyl, ((hydroxyalkyl)alkoxy)alkoxy, or ((alkoxy)alkoxy)alkoxy;
$R^{10}$ is hydrogen, alkyl, cycloalkyl, alkylcarbonyl, or alkoxycarbonyl;
$R^{11}$ is hydrogen or alkyl;
or $R^{10}$ and $R^{11}$ taken together with the nitrogen to which they are attached is azetidinyl, pyrrolidinyl, piperidinyl, piperazinyl, or morpholinyl, and is substituted with 0-2 substituents selected from alkyl, alkylcarbonyl, and alkoxycarbonyl;
$R^{12}$ is hydrogen or alkyl;
$R^{13}$ is hydrogen, alkyl, cycloalkyl, alkylcarbonyl, or alkoxycarbonyl;
$R^{14}$ is hydrogen or alkyl;
or $R^{13}$ and $R^{14}$ taken together with the nitrogen to which they are attached is azetidinyl, pyrrolidinyl, piperidinyl, piperazinyl, or morpholinyl, and is substituted with 0-2 substituents selected from alkyl, alkylcarbonyl, and alkoxycarbonyl;
L is alkylene, cycloalkylene, (cycloalkyl)alkyl, (alkyl)cycloalkyl, or alkyl(cycloalkyl)alkyl, and is substituted with 0-2 substituents selected from alkoxy, hydroxy, $CO_2R^{12}$ and $CONR^{13}R^{14}$;
$Ar^1$ is phenyl, pyridinyl or pyrimidinyl, and is substituted with 1 $CON(R^5)(R^6)$ and with 0-3 substituents selected from halo, alkyl, haloalkyl, alkoxy, and haloalkoxy;
$Ar^2$ is phenyl substituted with 0-3 substituents selected from halo, alkyl, haloalkyl, alkoxy, and haloalkoxy;
$Ar^3$ is phenyl, indanyl, fluorenyl, biphenyl, terphenyl, pyridinyl, pyrazolyl, isoxazolyl, isothiazolyl, imidazolyl, oxazolyl, thiazolyl, triazolyl, oxadiazolyl, thiadiazolyl, benzoxazolyl, indolinyl, or dibenzofuranyl, and is substituted with 0-3 substituents selected from cyano, halo, alkyl, alkenyl, haloalkyl, cycloalkyl, $(CO_2R^{12})$alkyl, $(CO_2R^{12})$alkenyl, $(CON(R^{13})(R^{14}))$alkyl, phenyl, hydroxyl, alkoxy, haloalkoxy, alkylcarbonyl, $CO_2R^{12}$, and $CON(R^{13})(R^{14})$;
or $Ar^3$ is phenyl substituted with 1 substituent selected from benzyl, tetrazolyloxy, thiazolyl, phenylpyrazolyl, methyloxadiazolyl, thiadiazolyl, triazolyl, methyltriazolyl, tetrazolyl, pyridinyl, and dimethoxypyrimdinyl; and
$Ar^4$ is phenyl, indanyl, tetrahydronaphthyl, isochromanyl, benzodioxolyl, pyridinyl, pyrazolyl, imidazolyl, or triazolyl and is substituted with 0-3 substituents selected from cyano, halo, alkyl, alkyenyl, haloalkyl, alkoxy, and haloalkoxy, $N(R^{13})(R^{14})$, and alkylCO;
or a pharmaceutically acceptable salt thereof.

Another aspect of the invention is a compound of formula I where
X and Y are N and Z is CH;
$R^1$ is haloalkyl;
$R^2$ is $(Ar^2)$alkyl;
$R^3$ is hydrogen;
$R^4$ is hydrogen;
$R^5$ is

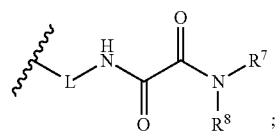

$R^6$ is hydrogen or alkyl;
$R^7$ is hydrogen, alkyl, cycloalkyl, or $Ar^3$;
$R^8$ is hydrogen or alkyl;
or $R^7$ and $R^8$ taken together with the nitrogen to which they are attached is piperidinyl, morpholinyl, or tetrahydroisoquinolinyl;
L is alkylene;
$Ar^1$ is pyridinyl substituted with 1 $CON(R^5)(R^6)$;
$Ar^2$ is phenyl substituted with 0-3 halo substituents; and
$Ar^3$ is phenyl, isoxazolyl, thiazolyl, or thiadiazolyl, and is substituted with 0-3 substituents selected from cyano, halo, alkyl, haloalkyl, alkoxy, and haloalkoxy;
or a pharmaceutically acceptable salt thereof Another aspect of the invention is a compound of formula I where $R^1$ is haloalkyl; $R^2$ is $(Ar^2)$alkyl; $R^3$ is hydrogen; $R^4$ is hydrogen; $R^7$ is hydrogen, alkyl, cycloalkyl, or $Ar^3$; L is

$Ar^1$ is phenyl substituted with 1 $CON(R^5)(R^6)$; $Ar^2$ is phenyl substituted with 1 halo; and $Ar^3$ is phenyl, isoxazolyl, thiazolyl, or thiadiazolyl, and is substituted with 0-1 substituents selected from cyano, halo, and alkyl; or a pharmaceutically acceptable salt thereof Another aspect of the invention is a compound of formula I where $R^1$ is haloalkyl or a pharmaceutically acceptable salt thereof.

Another aspect of the invention is a compound of formula I where $R^1$ is trifluroethyl or a pharmaceutically acceptable salt thereof.

Another aspect of the invention is a compound of formula I where $R^2$ is $(Ar^2)$alkyl or $(Ar^2)$cycloalkyl, or a pharmaceutically acceptable salt thereof.

Another aspect of the invention is a compound of formula I where $R^3$ is hydrogen and $R^4$ is hydrogen, or a pharmaceutically acceptable salt thereof.

Another aspect of the invention is a compound of formula I where $R^7$ is hydrogen, alkyl, cycloalkyl, or $Ar^3$; $R^8$ is hydrogen or alkyl; or $R^7$ and $R^8$ taken together with the nitrogen to which they are attached is piperidinyl, morpholinyl, or tetrahydroisoquinolinyl; or a pharmaceutically acceptable salt thereof.

Another aspect of the invention is a compound of formula I where $R^7$ is $Ar^3$ or a pharmaceutically acceptable salt thereof.

Another aspect of the invention is a compound of formula I where L is

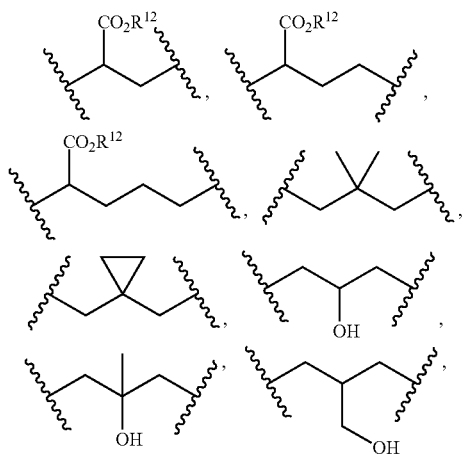

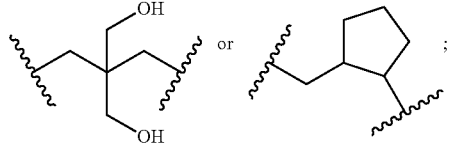

or a pharmaceutically acceptable salt thereof.

Another aspect of the invention is a compound of formula I where $Ar^1$ is pyridinyl substituted with 1 $CON(R^5)(R^6)$, or a pharmaceutically acceptable salt thereof. Another aspect of the invention is a compound of formula I where $R^1$ is alkyl, hydroxyalkyl, alkoxyalkyl, haloalkyl, cycloalkyl, hydroxycycloalkyl, alkoxycycloalkyl, halocycloalkyl, cycloalkenyl, benzyl, indanyl, or alkylcarbonyl.

Another aspect of the invention is a compound of formula I where $R^2$ is alkyl, $(Ar^2)$alkyl, $(Ar^2)$cycloalkyl, $((Ar^2)$cycloalkyl)alkyl, $((Ar^2)$alkyl)cycloalkyl, or $(((Ar^2)$alkyl)cycloalkyl)alkyl.

Another aspect of the invention is a compound of formula I where $R^3$ is hydrogen or alkyl.

Another aspect of the invention is a compound of formula I where $R^3$ is hydrogen.

Another aspect of the invention is a compound of formula I where $R^4$ is hydrogen or alkyl.

Another aspect of the invention is a compound of formula I where $R^4$ is hydrogen.

Another aspect of the invention is a compound of formula I where $R^5$ is

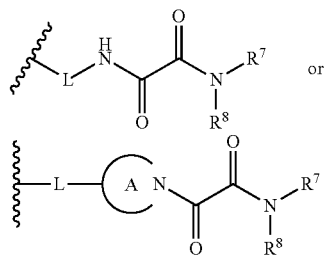

where ring A is a 4 to 7 membered alkylene ring substituted with L.

Another aspect of the invention is a compound of formula I where $R^6$ is hydrogen or alkyl.

Another aspect of the invention is a compound of formula I where $R^7$ is alkyl, cycloalkyl, (cycloalkyl)alkyl, (alkyl)cycloalkyl, ((alkyl))cycloalkyl)alkyl, or a bridged bicycloalkyl, and is substituted with 0-4 substituents selected from the group consisting of halo, alkyl, cycloalkyl, hydroxyalkyl, alkoxyalkyl, hydroxy, alkoxy, benzyloxy, $CO_2R^9$, $N(R^{10})(R^{11})$, tetrahydrofuranyl, tetrahydropyranyl, and $Ar^4$.

Another aspect of the invention is a compound of formula I where $R^7$ is hydrogen, N-alkoxycarbonylpiperidinyl, piperidinonyl, or $Ar^3$.

Another aspect of the invention is a compound of formula I where $R^8$ is hydrogen or alkyl.

Another aspect of the invention is a compound of formula I where $R^7$ and $R^8$ taken together with the nitrogen to which they are attached is azetidinyl, pyrrolidinyl, piperidinyl, piperazinyl, or morpholinyl, and is substituted with 0-2 substituents selected from alkyl, alkylcarbonyl, and alkoxycarbonyl.

Another aspect of the invention is a compound of formula I where $R^9$ is hydrogen, alkyl, hydroxyalkyl, alkoxyalkyl, ((hydroxyalkyl)alkoxy)alkoxy, or ((alkoxy)alkoxy)alkoxy.

Another aspect of the invention is a compound of formula I where $R^{19}$ is hydrogen, alkyl, cycloalkyl, alkylcarbonyl, or alkoxycarbonyl.

Another aspect of the invention is a compound of formula I where $R^{11}$ is hydrogen, alkyl.

Another aspect of the invention is a compound of formula I where $R^{10}$ and $R^{11}$ taken together with the nitrogen to which they are attached is azetidinyl, pyrrolidinyl, piperidinyl, piperazinyl, or morpholinyl, and is substituted with 0-2 substituents selected from alkyl, alkylcarbonyl, and alkoxycarbonyl.

Another aspect of the invention is a compound of formula I where $R^{12}$ is hydrogen or alkyl.

Another aspect of the invention is a compound of formula I where $R^{13}$ is hydrogen, alkyl, cycloalkyl, alkylcarbonyl, or alkoxycarbonyl.

Another aspect of the invention is a compound of formula I where $R^{14}$ is hydrogen or alkyl;

Another aspect of the invention is a compound of formula I where $R^{13}$ and $R^{14}$ taken together with the nitrogen to which they are attached is azetidinyl, pyrrolidinyl, piperidinyl, piperazinyl, or morpholinyl, and is substituted with 0-2 substituents selected from alkyl, alkylcarbonyl, and alkoxycarbonyl.

Another aspect of the invention is a compound of formula I where L is alkylene, cycloalkylene, (cycloalkyl)alkyl, (alkyl)cycloalkyl, or alkyl(cycloalkyl)alkyl, and is substituted with 0-1 $CO_2R^{12}$ or $CONR^{13}R^{14}$.

Another aspect of the invention is a compound of formula I where $Ar^1$ is phenyl, pyridyl or pyrimidinyl substituted with 1 $CON(R^5)(R^6)$ or $OR^5$ or $N(R^5)(R^6)$ and with 0-3 substituents selected from halo, alkyl, haloalkyl, alkoxy, and haloalkoxy.

Another aspect of the invention is a compound of formula I where $Ar^2$ is phenyl substituted with 0-3 substituents selected from halo, alkyl, haloalkyl, alkoxy, and haloalkoxy.

Another aspect of the invention is a compound of formula I where $Ar^3$ is phenyl, indanyl, fluorenyl, biphenyl, terphenyl, pyridinyl, pyrazolyl, isoxazolyl, imidazolyl, thiazolyl, triazolyl, thiadiazolyl, benzoxazolyl, indolinyl, or dibenzofuranyl, and is substituted with 0-3 substituents selected from cyano, halo, alkyl, alkenyl, haloalkyl, cycloalkyl, $(CO_2R^{12})$alkyl, $(CO_2R^{12})$alkenyl, $(CON(R^{13})(R^{14}))$alkyl, phenyl, hydroxyl, alkoxy, haloalkoxy, alkylcarbonyl, $CO_2R^{12}$, $CON(R^{13})(R^{14})$, or $PhCONHSO_2$.

Another aspect of the invention is a compound of formula I where $Ar^3$ is phenyl substituted with 1 substituents selected from benzyl, tetrazolyloxy, thiazolyl, phenylpyrazolyl, methyloxadiazolyl, thiadiazolyl, triazolyl, methyltriazolyl, tetrazolyl, pyridinyl, and dimethoxypyrimdinyl.

Another aspect of the invention is a compound of formula I where $Ar^4$ is phenyl, indanyl, tetrahydronaphthyl, isochromanyl, benzodioxolyl, pyridinyl, pyrazolyl, or imidazolyl, triazolyl and is substituted with 0-3 substituents selected from cyano, halo, alkyl, alkyenyl, haloalkyl, alkoxy, and haloalkoxy, $N(R^{13})(R^{14})$, and alkylCO.

Another aspect of the invention is a compound of formula I where $R^1$ is haloalkyl or a pharmaceutically acceptable salt thereof.

Another aspect of the invention is a compound of formula I where $R^1$ is trifluroethyl or a pharmaceutically acceptable salt thereof.

Another aspect of the invention is a compound of formula I where $R^2$ is $(Ar^2)$alkyl or $(Ar^2)$cycloalkyl, or a pharmaceutically acceptable salt thereof.

Another aspect of the invention is a compound of formula I where $R^2$ is $(Ar^2)$alkyl or $(Ar^2)$cycloalkyl, or a pharmaceutically acceptable salt thereof.

Another aspect of the invention is a compound of formula I where $R^7$ is alkyl, cycloalkyl, (cycloalkyl)alkyl, (alkyl) cycloalkyl, ((alkyl))cycloalkyl)alkyl, or a bridged bicycloalkyl, and is substituted with 0-4 substituents selected from the group consisting of halo, alkyl, cycloalkyl, hydroxyalkyl, alkoxyalkyl, hydroxy, alkoxy, benzyloxy, $CO_2R^9$, $N(R^{10})(R^{11})$, tetrahydrofuranyl, tetrahydropyranyl, and $Ar^4$; or a pharmaceutically acceptable salt thereof.

Another aspect of the invention is a compound of formula I where $R^7$ is $Ar^3$ or a pharmaceutically acceptable salt thereof.

Another aspect of the invention is a compound of formula I where L is

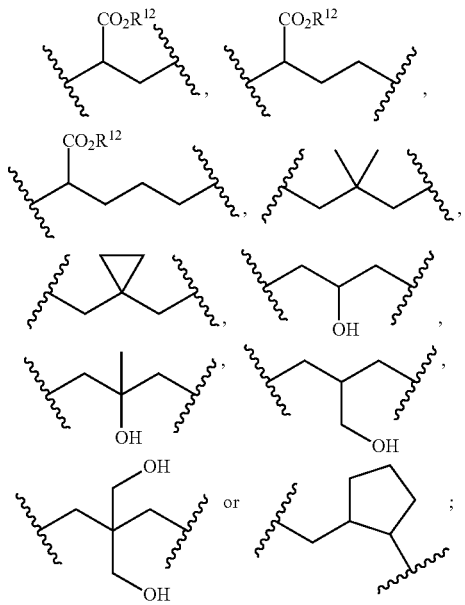

or a pharmaceutically acceptable salt thereof.

Any scope of any variable, including $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, L, $Ar^1$, $Ar^2$, $Ar^3$, and $Ar^4$, can be used independently with the scope of any other instance of a variable.

Unless specified otherwise, these terms have the following meanings "Halo" means fluoro, chloro, bromo, or iodo. "Alkyl" means a straight or branched alkyl group composed of 1 to 6 carbons. "Alkenyl" means a straight or branched alkyl group composed of 2 to 6 carbons with at least one double bond. "Cycloalkyl" means a monocyclic ring system composed of 3 to 8 carbons. "Alkylene" means a straight or branched divalent alkyl group. "Alkenylene" means a straight or branched divalent alkyl group with at least one double bond. "Cycloalkylene" means a divalent cycloalkane moiety composed of 3 to 7 carbons and includes gem-divalency (for example 1,1-cyclopropanediyl) as well as non-gem-divalency (for example, 1,4-cyclohexanediyl). "Alkylidinyl" means a divalent alkene substituent where the divalency occurs on the same carbon of the alkene. "Hydroxyalkyl," "alkoxy" and other terms with a substituted alkyl moiety include straight and branched isomers composed of 1 to 6 carbon atoms for the alkyl moiety. "Haloalkyl" and "haloalkoxy" include all halogenated isomers from monohalo substituted alkyl to perhalo substituted alkyl. "Aryl" includes carbocyclic and heterocyclic aromatic substituents. Phenylene is a divalent benzene ring. "1,4-Phenylene" means 1,4-benzenediyl with respect to regiochemistry for the divalent moiety. Parenthetic and multiparenthetic terms are intended to clarify bonding relationships to those skilled in the art. For example, a term such as ((R)alkyl) means an alkyl substituent further substituted with the substituent R.

The substituents described above may be attached at any suitable point of attachment unless otherwise specified. However, it is understood that the compounds encompassed by the present invention are those that are chemically stable as understood by those skilled in the art. Additionally, the compounds encompassed by the present disclosure are those that are suitably stable for use as a pharmaceutical agent.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, camsylate, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention possess asymmetric carbon atoms (see, for example, the structures below). The invention includes all stereoisomeric forms, including enantiomers and diastereomers as well as mixtures of stereoisomers such as racemates. Some stereoisomers can be made using methods known in the art. Stereoisomeric mixtures of the compounds and related intermediates can be separated into individual isomers according to methods commonly known in the art. The use of wedges or hashes in the depictions of molecular structures in the following schemes and tables is intended only to indicate relative stereochemistry, and should not be interpreted as implying absolute stereochemical assignments.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Biological Methods

Infection assays. HCV pseudoparticles, produced using standardized methodology (Bartosch, B., Dubuisson, J. and Cosset, F.-L. *J. Exp. Med.* 2003, 197:633-642) were made via a liposome-based transfection procedure of 293T cells with plasmids expressing the murine leukemia virus capsid and polymerase proteins, an MLV genome encoding the luciferase reporter gene, and envelope glycoproteins from either HCV or vesicular stomatitis virus (VSV). The genotype 1a HCV E1 and E2 envelope coding sequences were derived from the H77C isolate (GenBank accession number AF009606). Media containing pseudoparticles was collected 3 days following transfection, filtered, and stored at −20° C. as a viral stock. Infections were performed in 384-well plates by mixing pseudovirus with $1 \times 10^4$ Huh7 cells/well in the presence or absence of test inhibitors, followed by incubation at 37° C. Luciferase activity, reflecting the degree of entry of the pseudoparticles into host cells, was measured 2 days after infection. The specificity of the compounds for inhibiting HCV was determined by evaluating inhibition of VSV pseudoparticle infection.

Compounds and data analysis. Test compounds were serially diluted 3-fold in dimethyl sulfoxide (DMSO) to give a final concentration range in the assay of 50.0 µM to 0.04 µM. Maximum activity (100% of control) and background were derived from control wells containing DMSO but no inhibitor or from uninfected wells, respectively. The individual signals in each of the compound test wells were then divided by the averaged control values after background subtraction and multiplied by 100% to determine percent activity. Assays were performed in duplicate and average $EC_{50}$ values (reflecting the concentration at which 50% inhibition of virus replication was achieved) were calculated. Compound $EC_{50}$ data is expressed as A=0.01≤10 nM; B=10-1000 nM. Representative data for compounds are reported in Table 1.

TABLE 1

| Example | Structure | $EC_{50}$ (nM) 1a (H77C) | $EC_{50}$ (nM) 1a (H77C) |
|---------|-----------|--------------------------|--------------------------|
| 1001    | 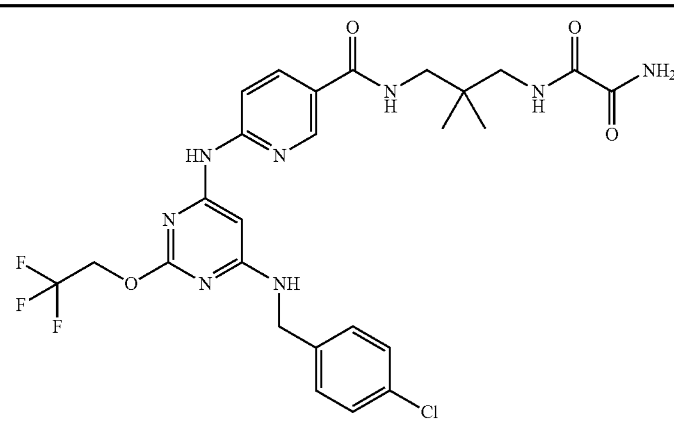          | 1.465                    | A                        |

TABLE 1-continued

| Example | Structure | EC$_{50}$ (nM) 1a (H77C) | EC$_{50}$ (nM) 1a (H77C) |
|---|---|---|---|
| 1002 | 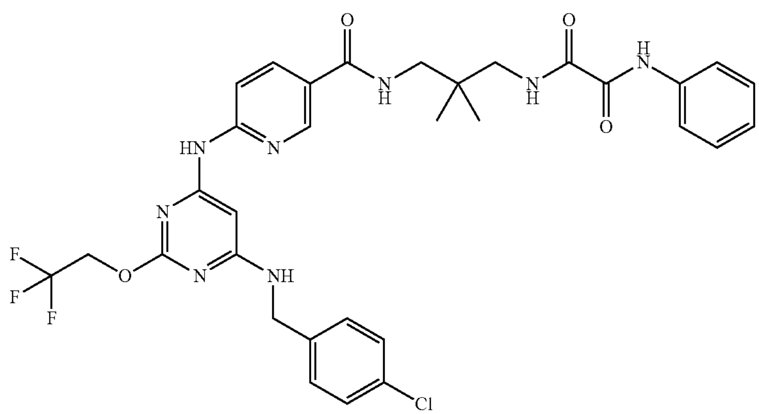 [SMILES: CC(C)(CNC(=O)C(=O)Nc1ccccc1)CNC(=O)c1ccc(Nc2cc(NCc3ccc(Cl)cc3)nc(OCC(F)(F)F)n2)nc1] | | A |
| 1003 | 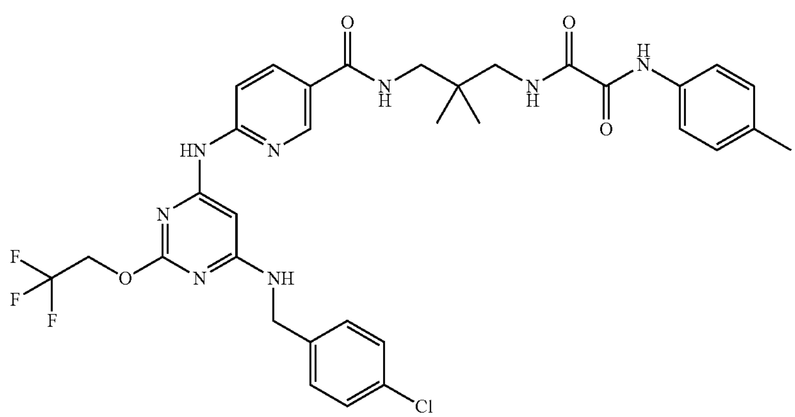 [SMILES: Cc1ccc(NC(=O)C(=O)NCC(C)(C)CNC(=O)c2ccc(Nc3cc(NCc4ccc(Cl)cc4)nc(OCC(F)(F)F)n3)nc2)cc1] | 0.214 | A |
| 1004 | 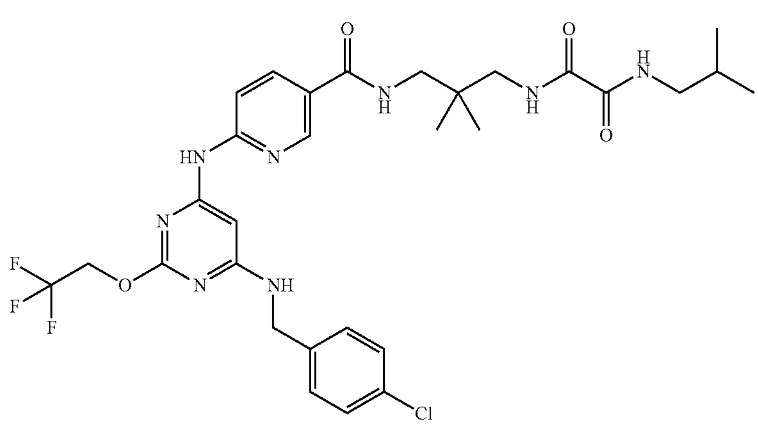 [SMILES: CC(C)CNC(=O)C(=O)NCC(C)(C)CNC(=O)c1ccc(Nc2cc(NCc3ccc(Cl)cc3)nc(OCC(F)(F)F)n2)nc1] | | A |

TABLE 1-continued

| Example | Structure | EC$_{50}$ (nM) 1a (H77C) | EC$_{50}$ (nM) 1a (H77C) |
|---|---|---|---|
| 1005 | 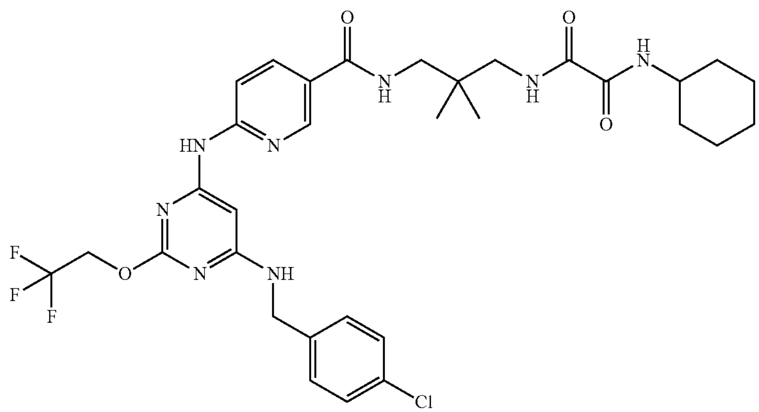 [SMILES: CC(C)(CNC(=O)C(=O)NC1CCCCC1)CNC(=O)c1ccc(Nc2cc(NCc3ccc(Cl)cc3)nc(OCC(F)(F)F)n2)nc1] | A | |
| 1006 | 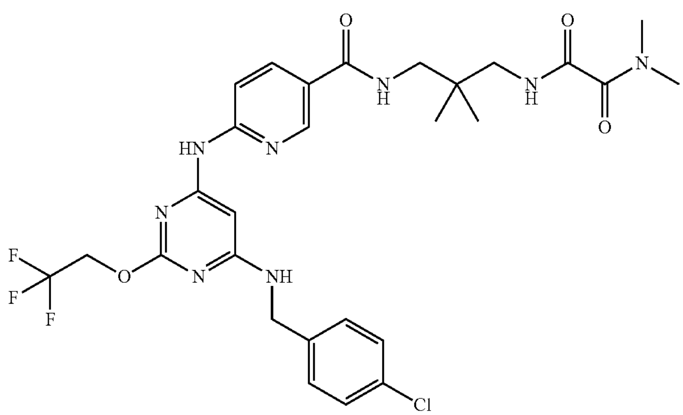 [SMILES: CN(C)C(=O)C(=O)NCC(C)(C)CNC(=O)c1ccc(Nc2cc(NCc3ccc(Cl)cc3)nc(OCC(F)(F)F)n2)nc1] | B | |
| 1007 | 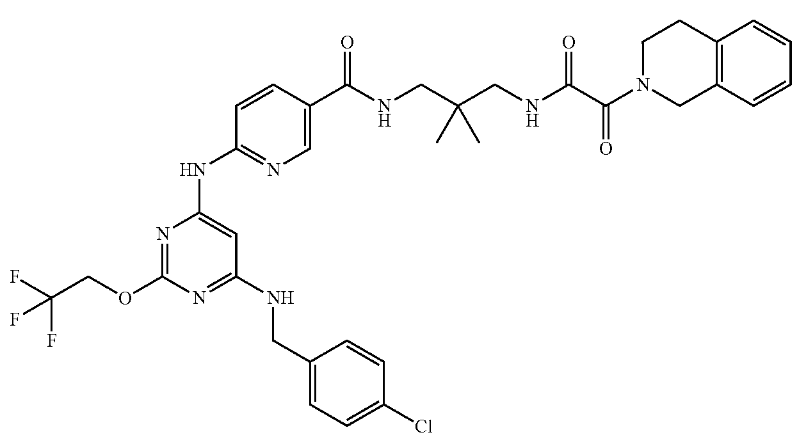 [SMILES: CC(C)(CNC(=O)C(=O)N1CCc2ccccc2C1)CNC(=O)c1ccc(Nc2cc(NCc3ccc(Cl)cc3)nc(OCC(F)(F)F)n2)nc1] | A | |

TABLE 1-continued

| Example | Structure | EC$_{50}$ (nM) 1a (H77C) | EC$_{50}$ (nM) 1a (H77C) |
|---|---|---|---|
| 1008 | 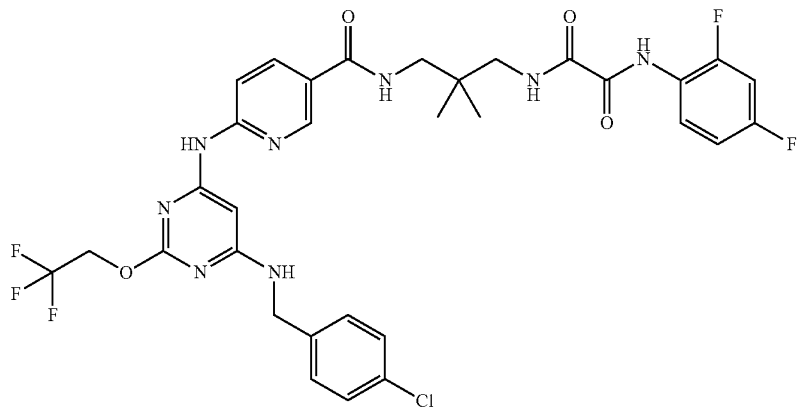 [SMILES: CC(C)(CNC(=O)C(=O)Nc1ccc(F)cc1F)CNC(=O)c1ccc(Nc2cc(NCc3ccc(Cl)cc3)nc(OCC(F)(F)F)n2)nc1] | A | |
| 1009 | 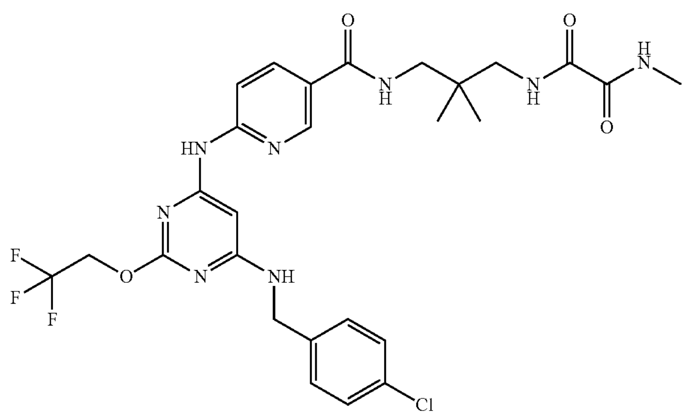 [SMILES: CNC(=O)C(=O)NCC(C)(C)CNC(=O)c1ccc(Nc2cc(NCc3ccc(Cl)cc3)nc(OCC(F)(F)F)n2)nc1] | A | |
| 1010 | 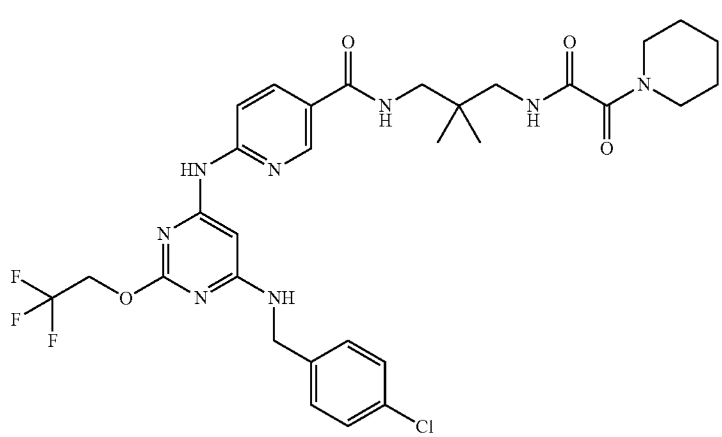 [SMILES: CC(C)(CNC(=O)C(=O)N1CCCCC1)CNC(=O)c1ccc(Nc2cc(NCc3ccc(Cl)cc3)nc(OCC(F)(F)F)n2)nc1] | B | |

TABLE 1-continued

| Example | Structure | EC$_{50}$ (nM) 1a (H77C) | EC$_{50}$ (nM) 1a (H77C) |
|---|---|---|---|
| 1011 | 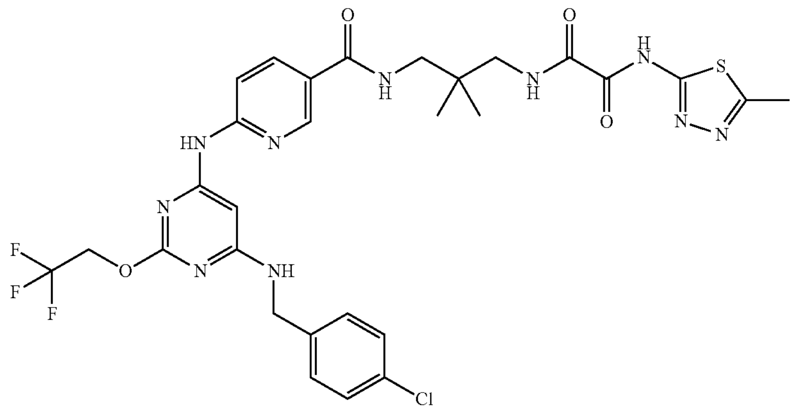 [SMILES: Cc1nnc(NC(=O)C(=O)NCC(C)(C)CNC(=O)c2ccc(Nc3cc(NCc4ccc(Cl)cc4)nc(OCC(F)(F)F)n3)nc2)s1] | | B |
| 1012 | 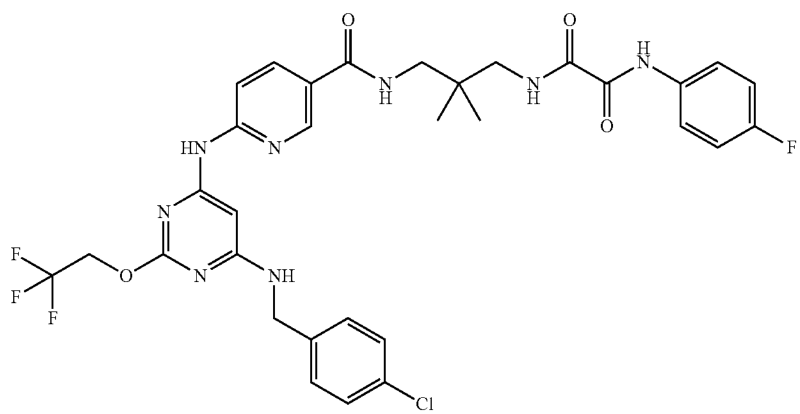 [SMILES: CC(C)(CNC(=O)C(=O)Nc1ccc(F)cc1)CNC(=O)c1ccc(Nc2cc(NCc3ccc(Cl)cc3)nc(OCC(F)(F)F)n2)nc1] | 0.482 | A |
| 1013 | 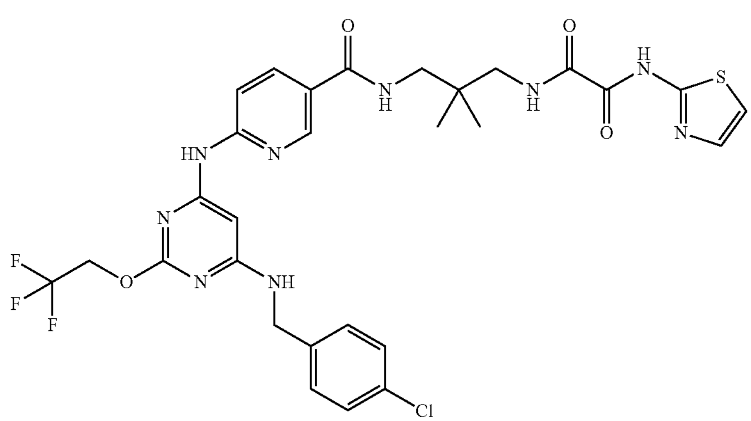 [SMILES: CC(C)(CNC(=O)C(=O)Nc1nccs1)CNC(=O)c1ccc(Nc2cc(NCc3ccc(Cl)cc3)nc(OCC(F)(F)F)n2)nc1] | | A |

TABLE 1-continued

| Example | Structure | EC$_{50}$ (nM) 1a (H77C) | EC$_{50}$ (nM) 1a (H77C) |
|---|---|---|---|
| 1014 | 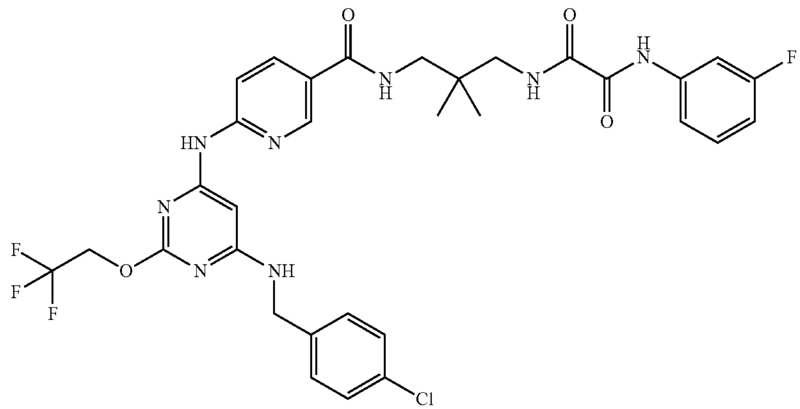 [SMILES: CC(C)(CNC(=O)C(=O)Nc1cccc(F)c1)CNC(=O)c1ccc(Nc2cc(NCc3ccc(Cl)cc3)nc(OCC(F)(F)F)n2)nc1] | | A |
| 1015 | 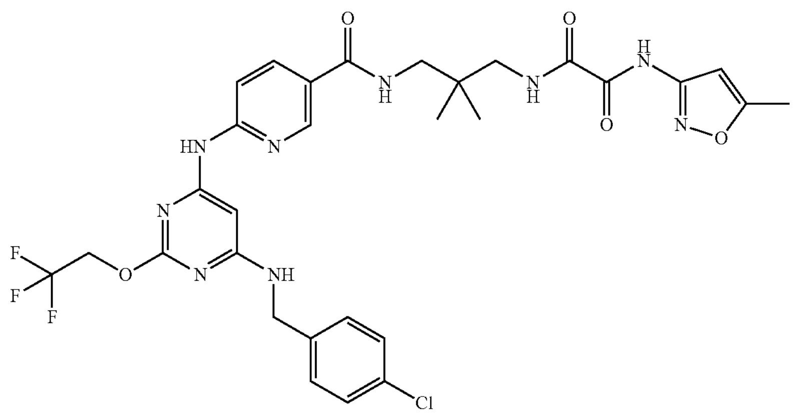 [SMILES: Cc1cc(NC(=O)C(=O)NCC(C)(C)CNC(=O)c2ccc(Nc3cc(NCc4ccc(Cl)cc4)nc(OCC(F)(F)F)n3)nc2)no1] | 1.309 | A |
| 1016 | 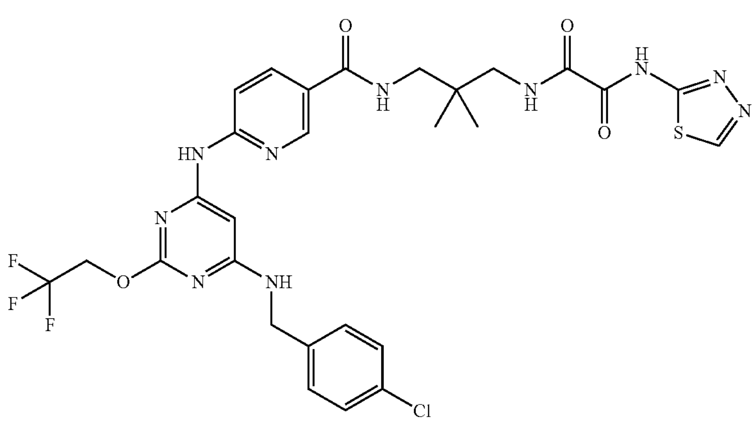 [SMILES: CC(C)(CNC(=O)C(=O)Nc1nncs1)CNC(=O)c1ccc(Nc2cc(NCc3ccc(Cl)cc3)nc(OCC(F)(F)F)n2)nc1] | 56.840 | B |

TABLE 1-continued

| Example | Structure | EC$_{50}$ (nM) 1a (H77C) | EC$_{50}$ (nM) 1a (H77C) |
|---|---|---|---|
| 1017 | 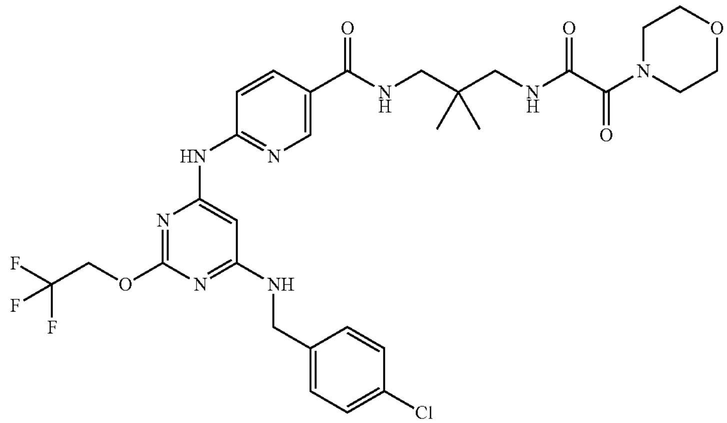 [SMILES: CC(C)(CNC(=O)C(=O)N1CCOCC1)CNC(=O)c1ccc(Nc2cc(NCc3ccc(Cl)cc3)nc(OCC(F)(F)F)n2)nc1] | 26.780 | B |
| 1018 | 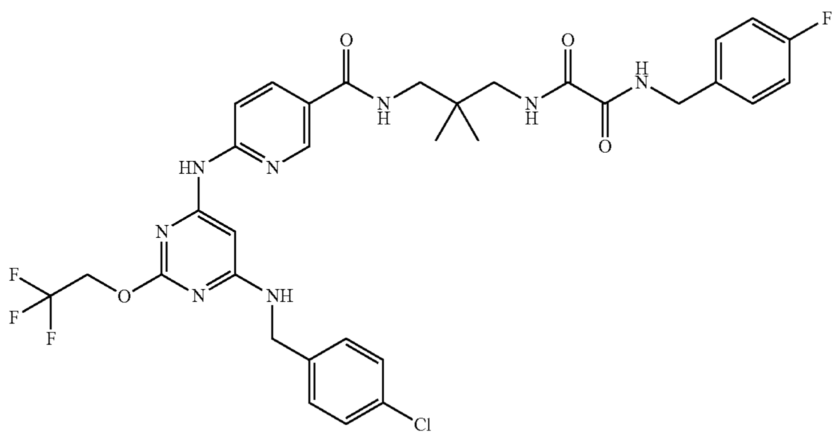 [SMILES: CC(C)(CNC(=O)C(=O)NCc1ccc(F)cc1)CNC(=O)c1ccc(Nc2cc(NCc3ccc(Cl)cc3)nc(OCC(F)(F)F)n2)nc1] | | A |
| 1019 | 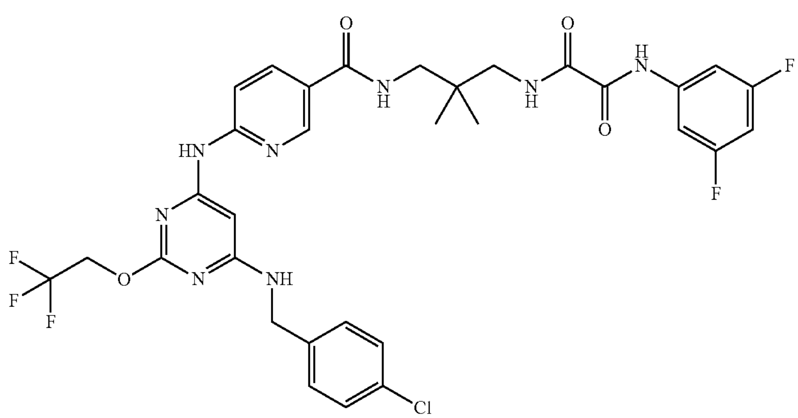 [SMILES: CC(C)(CNC(=O)C(=O)Nc1cc(F)cc(F)c1)CNC(=O)c1ccc(Nc2cc(NCc3ccc(Cl)cc3)nc(OCC(F)(F)F)n2)nc1] | | B |

TABLE 1-continued

| Example | Structure | EC$_{50}$ (nM) 1a (H77C) | EC$_{50}$ (nM) 1a (H77C) |
|---|---|---|---|
| 1020 | 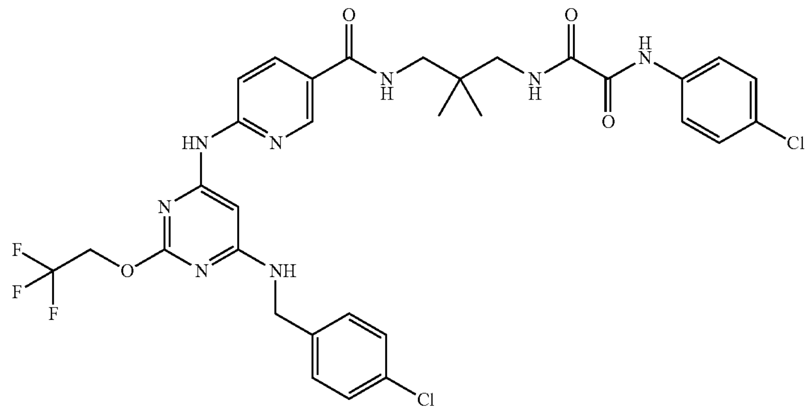 [SMILES: CC(C)(CNC(=O)C(=O)Nc1ccc(Cl)cc1)CNC(=O)c1ccc(Nc2cc(NCc3ccc(Cl)cc3)nc(OCC(F)(F)F)n2)nc1] | | A |

Pharmaceutical Compositions and Methods of Treatment

The compounds demonstrate activity against HCV NS5B and can be useful in treating HCV and HCV infection. Therefore, another aspect of the invention is a composition comprising a compound, or a pharmaceutically acceptable salt thereof, and a pharmaceutically acceptable carrier.

Another aspect of the invention is a composition further comprising a compound having anti-HCV activity.

Another aspect of the invention is a composition where the compound having anti-HCV activity is an interferon or a ribavirin. Another aspect of the invention is where the interferon is selected from interferon alpha 2B, pegylated interferon alpha, consensus interferon, interferon alpha 2A, interferon lambda, and lymphoblastoid interferon tau.

Another aspect of the invention is a composition where the compound having anti-HCV activity is a cyclosporin. Another aspect of the invention is where the cyclosporin is cyclosporin A.

Another aspect of the invention is a composition where the compound having anti-HCV activity is selected from the group consisting of interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is a composition where the compound having anti-HCV activity is effective to inhibit the function of a target selected from HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is a composition comprising a compound, or a pharmaceutically acceptable salt thereof, a pharmaceutically acceptable carrier, an interferon and ribavirin.

Another aspect of the invention is a method of inhibiting the function of the HCV replicon comprising contacting the HCV replicon with a compound or a pharmaceutically acceptable salt thereof Another aspect of the invention is a method of inhibiting the function of the HCV NS5B protein comprising contacting the HCV NS5B protein with a compound or a pharmaceutically acceptable salt thereof.

Another aspect of the invention is a method of treating an HCV infection in a patient comprising administering to the patient a therapeutically effective amount of a compound or a pharmaceutically acceptable salt thereof. In another embodiment the compound is effective to inhibit the function of the HCV replicon. In another embodiment the compound is effective to inhibit the function of the HCV NS5B protein.

Another aspect of the invention is a method of treating an HCV infection in a patient comprising administering to the patient a therapeutically effective amount of a compound, or a pharmaceutically acceptable salt thereof, in conjunction with (prior to, after, or concurrently) another compound having anti-HCV activity.

Another aspect of the invention is the method where the other compound having anti-HCV activity is an interferon or a ribavirin.

Another aspect of the invention is the method where the interferon is selected from interferon alpha 2B, pegylated interferon alpha, consensus interferon, interferon alpha 2A, interferon lambda, and lymphoblastoid interferon tau.

Another aspect of the invention is the method where the other compound having anti-HCV activity is a cyclosporin.

Another aspect of the invention is the method where the cyclosporin is cyclosporin A.

Another aspect of the invention is the method where the other compound having anti-HCV activity is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is the method where the other compound having anti-HCV activity is effective to inhibit the function of a target selected from the group consisting of HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is the method where the other compound having anti-HCV activity is effective to inhibit the function of target in the HCV life cycle other than the HCV NS5B protein.

"Therapeutically effective" means the amount of agent required to provide a meaningful patient benefit as understood by practitioners in the field of hepatitis and HCV infection.

"Patient" means a person infected with the HCV virus and suitable for therapy as understood by practitioners in the field of hepatitis and HCV infection.

"Treatment," "therapy," "regimen," "HCV infection," and related terms are used as understood by practitioners in the field of hepatitis and HCV infection.

The compounds of this invention are generally given as pharmaceutical compositions comprised of a therapeutically effective amount of a compound or its pharmaceutically acceptable salt and a pharmaceutically acceptable carrier and may contain conventional excipients. Pharmaceutically acceptable carriers are those conventionally known carriers having acceptable safety profiles. Compositions encompass all common solid and liquid forms including for example capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions. See, for example, *Remington's Pharmaceutical Sciences*, Mack Publishing Company, Easton, Pa., 17th edition, 1985.

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other agents will be present in a unit range similar to agents of that class used clinically. Typically, this is 1-100 mg/mL.

The invention encompasses all conventional modes of administration; oral and parenteral methods are preferred. Generally, the dosing regimen will be similar to other agents used clinically. Typically, the daily dose will be 1-100 mg/kg body weight daily. Generally, more compound is required orally and less parenterally. The specific dosing regime, however, will be determined by a physician using sound medical judgement.

The invention also encompasses methods where the compound is given in combination therapy. That is, the compound can be used in conjunction with, but separately from, other agents useful in treating hepatitis and HCV infection. In these combination methods, the compound will generally be given in a daily dose of 1-100 mg/kg body weight daily in conjunction with other agents. The other agents generally will be given in the amounts used therapeutically. The specific dosing regime, however, will be determined by a physician using sound medical judgement.

Some examples of compounds suitable for compositions and methods are listed in Table 2.

TABLE 2

| Brand Name | Physiological Class | Type of Inhibitor or Target | Source Company |
|---|---|---|---|
| NIM811 | | Cyclophilin Inhibitor | Novartis |
| Zadaxin | | Immuno-modulator | Sciclone |
| Suvus | | Methylene blue | Bioenvision |
| Actilon (CPG10101) | | TLR9 agonist | Coley |
| Batabulin (T67) | Anticancer | β-tubulin inhibitor | Tularik Inc., South San Francisco, CA |
| ISIS 14803 | Antiviral | antisense | ISIS Pharmaceuticals Inc, Carlsbad, CA/Elan Phamaceuticals Inc., New York, NY |
| Summetrel | Antiviral | antiviral | Endo Pharmaceuticals Holdings Inc., Chadds Ford, PA |
| GS-9132 (ACH-806) | Antiviral | HCV Inhibitor | Achillion/Gilead |
| Pyrazolopyrimidine compounds and salts From WO-2005047288 May 26, 2005 | Antiviral | HCV Inhibitors | Arrow Therapeutics Ltd. |
| Levovirin | Antiviral | IMPDH inhibitor | Ribapharm Inc., Costa Mesa, CA |
| Merimepodib (VX-497) | Antiviral | IMPDH inhibitor | Vertex Pharmaceuticals Inc., Cambridge, MA |
| XTL-6865 (XTL-002) | Antiviral | monoclonal antibody | XTL Biopharmaceuticals Ltd., Rehovot, Isreal |
| Telaprevir (VX-950, LY-570310) | Antiviral | NS3 serine protease inhibitor | Vertex Pharmaceuticals Inc., Cambridge, MA/Eli Lilly and Co. Inc., Indianapolis, IN |

TABLE 2-continued

| Brand Name | Physiological Class | Type of Inhibitor or Target | Source Company |
|---|---|---|---|
| HCV-796 | Antiviral | NS5B Replicase Inhibitor | Wyeth/Viropharma |
| NM-283 | Antiviral | NS5B Replicase Inhibitor | Idenix/Novartis |
| GL-59728 | Antiviral | NS5B Replicase Inhibitor | Gene Labs/Novartis |
| GL-60667 | Antiviral | NS5B Replicase Inhibitor | Gene Labs/Novartis |
| 2'C MeA | Antiviral | NS5B Replicase Inhibitor | Gilead |
| PSI 6130 | Antiviral | NS5B Replicase Inhibitor | Roche |
| R1626 | Antiviral | NS5B Replicase Inhibitor | Roche |
| 2'C Methyl adenosine | Antiviral | NS5B Replicase Inhibitor | Merck |
| JTK-003 | Antiviral | RdRp inhibitor | Japan Tobacco Inc., Tokyo, Japan |
| Levovirin | Antiviral | ribavirin | ICN Pharmaceuticals, Costa Mesa, CA |
| Ribavirin | Antiviral | ribavirin | Schering-Plough Corporation, Kenilworth, NJ |
| Viramidine | Antiviral | Ribavirin Prodrug | Ribapharm Inc., Costa Mesa, CA |
| Heptazyme | Antiviral | ribozyme | Ribozyme Pharmaceuticals Inc., Boulder, CO |
| BILN-2061 | Antiviral | serine protease inhibitor | Boehringer Ingelheim Pharma KG, Ingelheim, Germany |
| SCH 503034 | Antiviral | serine protease inhibitor | Schering Plough |
| Zadazim | Immune modulator | Immune modulator | SciClone Pharmaceuticals Inc., San Mateo, CA |
| Ceplene | Immunomodulator | immune modulator | Maxim Pharmaceuticals Inc., San Diego, CA |
| CellCept | Immunosuppressant | HCV IgG immunosuppressant | F. Hoffmann-La Roche LTD, Basel, Switzerland |
| Civacir | Immunosuppressant | HCV IgG immunosuppressant | Nabi Biopharmaceuticals Inc., Boca Raton, FL |
| Albuferon-α | Interferon | albumin IFN-α2b | Human Genome Sciences Inc., Rockville, MD |
| Infergen A | Interferon | IFN alfacon-1 | InterMune Pharmaceuticals Inc., Brisbane, CA |
| Omega IFN | Interferon | IFN-ω | Intarcia Therapeutics |
| IFN-β and EMZ701 | Interferon | IFN-β and EMZ701 | Transition Therapeutics Inc., Ontario, Canada |
| Rebif | Interferon | IFN-β1a | Serono, Geneva, Switzerland |
| Roferon A | Interferon | IFN-α2a | F. Hoffmann-La Roche LTD, Basel, Switzerland |
| Intron A | Interferon | IFN-α2b | Schering-Plough Corporation, Kenilworth, NJ |
| Intron A and Zadaxin | Interferon | IFN-α2b/α1-thymosin | RegeneRx Biopharma. Inc., Bethesda, MD/SciClone Pharmaceuticals Inc, San Mateo, CA |
| Rebetron | Interferon | IFN-α2b/ribavirin | Schering-Plough Corporation, Kenilworth, NJ |
| Actimmune | Interferon | INF-γ | InterMune Inc., Brisbane, CA |
| Interferon-β | Interferon | Interferon-β-1a | Serono |

TABLE 2-continued

| Brand Name | Physiological Class | Type of Inhibitor or Target | Source Company |
|---|---|---|---|
| Multiferon | Interferon | Long lasting IFN | Viragen/Valentis |
| Wellferon | Interferon | Lympho-blastoid IFN-αn1 | GlaxoSmithKline plc, Uxbridge, UK |
| Omniferon | Interferon | natural IFN-α | Viragen Inc., Plantation, FL |
| Pegasys | Interferon | PEGylated IFN-α2a | F. Hoffmann-La Roche LTD, Basel, Switzerland |
| Pegasys and Ceplene | Interferon | PEGylated IFN-α2a/immune modulator | Maxim Pharmaceuticals Inc., San Diego, CA |
| Pegasys and Ribavirin | Interferon | PEGylated IFN-α2a/ribavirin | F. Hoffmann-La Roche LTD, Basel, Switzerland |
| PEG-Intron | Interferon | PEGylated IFN-α2b | Schering-Plough Corporation, Kenilworth, NJ |
| PEG-Intron/Ribavirin | Interferon | PEGylated IFN-α2b/ribavirin | Schering-Plough Corporation, Kenilworth, NJ |
| IP-501 | Liver protection | antifibrotic | Indevus Pharmaceuticals Inc., Lexington, MA |
| IDN-6556 | Liver protection | caspase inhibitor | Idun Pharmaceuticals Inc., San Diego, CA |
| ITMN-191 (R-7227) | Antiviral | serine protease inhibitor | InterMune Pharmaceuticals Inc., Brisbane, CA |
| GL-59728 | Antiviral | NS5B Replicase Inhibitor | Genelabs |
| ANA-971 | Antiviral | TLR-7 agonist | Anadys |
| Boceprevir | Antiviral | serine protease inhibitor | Schering Plough |
| TMS-435 | Antiviral | serine protease inhibitor | Tibotec BVBA, Mechelen, Belgium |
| BI-201335 | Antiviral | serine protease inhibitor | Boehringer Ingelheim Pharma KG, Ingelheim, Germany |
| MK-7009 | Antiviral | serine protease inhibitor | Merck |
| PF-00868554 | Antiviral | replicase inhibitor | Pfizer |
| ANA598 | Antiviral | Non-Nucleoside NS5B Polymerase Inhibitor | Anadys Pharmaceuticals, Inc., San Diego, CA, USA |
| IDX375 | Antiviral | Non-Nucleoside Replicase Inhibitor | Idenix Pharmaceuticals, Cambridge, MA, USA |
| BILB 1941 | Antiviral | NS5B Polymerase Inhibitor | Boehringer Ingelheim Canada Ltd R&D, Laval, QC, Canada |
| PSI-7851 | Antiviral | Nucleoside Polymerase Inhibitor | Pharmasset, Princeton, NJ, USA |
| PSI-7977 | Antiviral | Nucleotide NS5B Polymerase Inhibitor | Pharmasset, Princeton, NJ, USA |
| VCH-759 | Antiviral | NS5B Polymerase Inhibitor | ViroChem Pharma |
| VCH-916 | Antiviral | NS5B Polymerase Inhibitor | ViroChem Pharma |
| GS-9190 | Antiviral | NS5B Polymerase Inhibitor | Gilead |
| Peg-interferon lamda | Antiviral | Interferon | ZymoGenetics/Bristol-Myers Squibb |

Synthetic Methods

The compounds may be made by methods known in the art including those described below and including variations within the skill of the art. Some reagents and intermediates are known in the art. Other reagents and intermediates can be made by methods known in the art using readily available materials. The variables (e.g. numbered "R" substituents) used to describe the synthesis of the compounds are intended only to illustrate how to make the compounds and are not to be confused with variables used in the claims or in other sections of the specification. The following methods are for illustrative purposes and are not intended to limit the scope of the invention.

Abbreviations used in the schemes generally follow conventions used in the art. Chemical abbreviations used in the specification and examples are defined as follows: "NaHMDS" for sodium bis(trimethylsilyl)amide; "DMF" for N,N-dimethylformamide; "MeOH" for methanol; "NBS" for N-bromosuccinimide; "Ar" for aryl; "TFA" for trifluoroacetic acid; "LAH" for lithium aluminum hydride; "BOC", "DMSO" for dimethylsulfoxide; "h" for hours; "rt" for room temperature or retention time (context will dictate); "min" for minutes; "EtOAc" for ethyl acetate; "THF" for tetrahydrofuran; "EDTA" for ethylenediaminetetraacetic acid; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine, "Nf" for $CF_3(CF_2)_3SO_2$—; and "TMOF" for trimethylorthoformate.

Abbreviations are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

LC/MS Method (i.e., compound identification). All Liquid Chromatography (LC) data were recorded on a Shimadzu LC-10AS or LC-20AS liquid chromatograph using a SPD-10AV or SPD-20A UV-Vis detector and Mass Spectrometry (MS) data were determined with a Micromass Platform for LC in electrospray mode.

HPLC Method (i.e., compound isolation). Compounds purified by preparative HPLC were diluted in methanol (1.2 mL) and purified using a Shimadzu LC-8A or LC-10A or Dionex APS-3000 or Waters Acquity™ automated preparative HPLC system.

Syntheses of Intermediates:
Preparation of Intermediates:

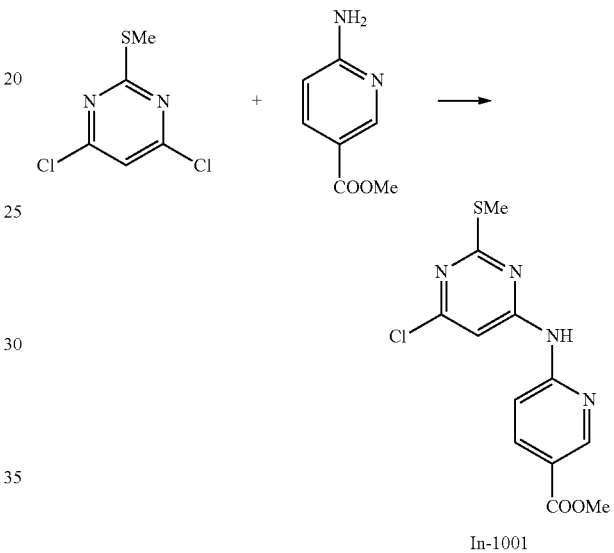

In-1001

NaHMDS (65.7 mL, 1M in THF) was added into the solution of 4,6-dichloro-2-(methylthio)pyrimidine (6.4 g) and methyl 4-aminobenzoate (5 g) in THF (200 mL). The reaction was stirred at room temperature for 16 hours, before being quenched by water. The aqueous layer was extracted with EtOAc (3×200 mL). The combined organic phase was dried over MgSO$_4$ and concentrated under vacuum to give the crude In-1001, methyl 6-((6-chloro-2-(methylthio)pyrimidin-4-yl)amino)nicotinate, which was used in the next step without purification.

| Methyl 6-(6-chloro-2-(methylthio)pyrimidin-4-ylamino)nicotinate Methyl 6-((6-chloro-2-(methylthio)pyrimidin-4-yl)amino)nicotinate | |
|---|---|
| MS (M + H)$^+$ Calcd. | 311.0 |
| MS (M + H)$^+$ Observ. | 311.1 |
| Retention Time | 1.83 minutes |
| LC Condition | |
| Solvent A | 5% ACN: 95% Water : 10 mM Ammonium Actetate |
| Solvent B | 95% ACN: 5% Water : 10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN: Water: Ammonium Actetate |
| Column | Phenomenex LUNA C18, 30x2, 3u |

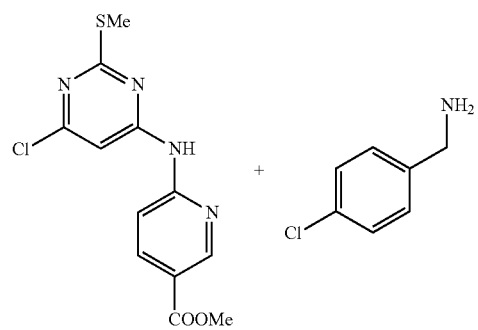

In-1001

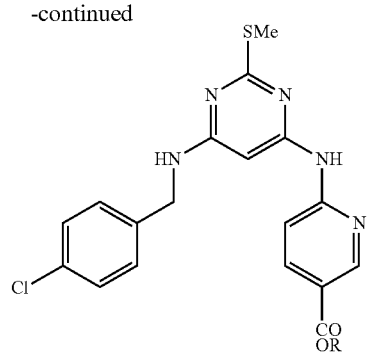

R = Me, In-1002a
R = Et, In-1002b

The mixture of ethyl 6-(6-chloro-2-(methylthio)pyrimidin-4-ylamino)nicotinate (500 mg) and (4-chlorophenyl)methanamine (1139 mg) in EtOH (20 mL) was heated to 115° C. for 4 hours, showing formation of ethyl 6-(6-(4-chlorobenzylamino)-2-(methylthio)pyrimidin-4-ylamino)nicotinate. After removal of solvents, the residue was purified by silica gele chromatography to give a mixture of methyl 6-((6-((4-chlorobenzyl)amino)-2-(methylthio)pyrimidin-4-yl)amino)nicotinate (In-1002a) and ethyl 6-((6-((4-chlorobenzyl)amino)-2-(methylthio)pyrimidin-4-yl)amino)nicotinate (In-1002b).

| methyl 6-((6-((4-chlorobenzyl)amino)-2-(methylthio)pyrimidin-4-yl)amino)nicotinate | |
|---|---|
| MS (M + H)+ Calcd. | 416.1 |
| MS (M + H)+ Observ. | 416.5 |
| Retention Time | 1.84 minutes |
| LC Condition | |
| Solvent A | 5% ACN: 95% Water: 10 mM Ammonium Actetate |
| Solvent B | 95% ACN: 5% Water: 10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN: Water: Ammonium Actetate |
| Column | Phenomenex LUNA C18, 30x2, 3u |

| ethyl 6-((6-((4-chlorobenzyl)amino)-2-(methylthio)pyrimidin-4-yl)amino)nicotinate | |
|---|---|
| MS (M + H)+ Calcd. | 430.1 |
| MS (M + H)+ Observ. | 430.4 |
| Retention Time | 2.06 minutes |
| LC Condition | |
| Solvent A | 5% ACN: 95% Water: 10 mM Ammonium Actetate |
| Solvent B | 95% ACN: 5% Water: 10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN: Water: Ammonium Actetate |
| Column | Phenomenex LUNA C18, 30x2, 3u |

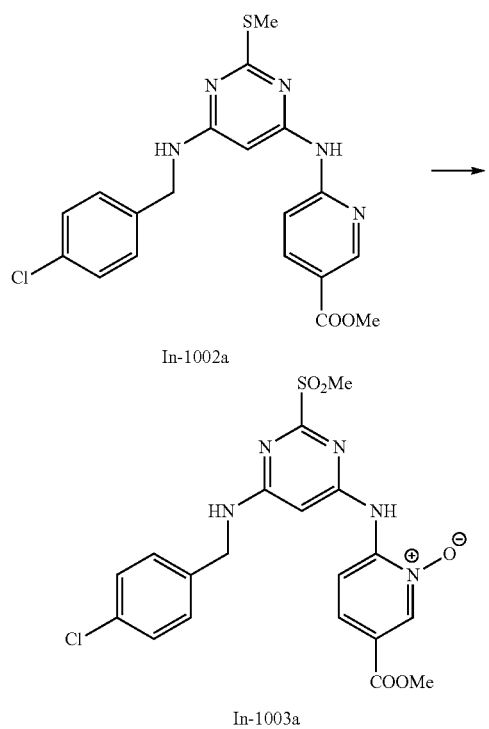

In-1002a

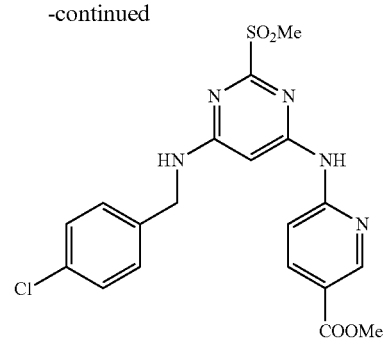

In-1003b mCPBA (2.91 g, 77%) was added into the solution of crude methyl 6-((6-((4-hydroxybenzyl)amino)-2-(methylthio)pyrimidin-4-yl)amino)nicotinate (1.8 g) in CH$_2$Cl$_2$ (100 mL). The reaction was stirred at room temperature for 48 hours to give 2-((6-((4-chlorobenzyl)amino)-2-(methylsulfonyl)pyrimidin-4-yl)amino)-5-(methoxycarbonyl)pyridine 1-oxide (In-1003a) and methyl 6-((6-((4-chlorobenzyl)amino)-2-(methylsulfonyl)pyrimidin-4-yl)amino)nicotinate (In-1003b), before being quenched by water. The aqueous layer was extracted with EtOAc (3×100 mL). The combined organic phase was dried over MgSO$_4$ and concentrated under vacuum to give the crude product which was used as was.

| 2-((6-((4-chlorobenzyp)amino)-2-(methylsulfonyl)pyrimidin-4-yl)amino)-5-(methoxycarbonyl)pyridine 1-oxide | |
|---|---|
| MS (M + H)$^+$ Calcd. | 464.1 |
| MS (M + H)$^+$ Observ. | 464.4 |
| Retention Time | 1.46 min |
| LC Condition | |
| Solvent A | 5 % ACN: 95% Water : 10mM Ammonium Actetate |
| Solvent B | 95 % ACN: 5% Water : 10mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN: Water: Ammonium Actetate |
| Column | Phenomenex LUNA C18, 30x2, 3u |

| methyl 6-((6-((4-chlorobenzyl)amino)-2-(methylsulfonyl)pyrimidin-4-yl)amino)nicotinate | |
|---|---|
| MS (M + H)$^+$ Calcd. | 448.1 |
| MS (M + H)$^+$ Observ. | 448.4 |
| Retention Time | 1.62 min |
| LC Condition | |
| Solvent A | 5 % ACN: 95% Water : 10mM Ammonium Actetate |
| Solvent B | 95 % ACN: 5% Water : 10mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN: Water: Ammonium Actetate |
| Column | Phenomenex LUNA C18, 30x2, 3u |

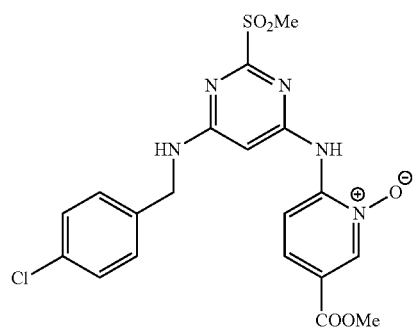

In-1003a

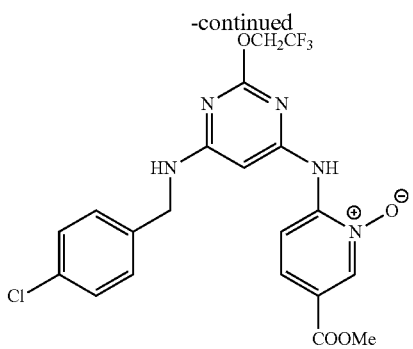

In-1004

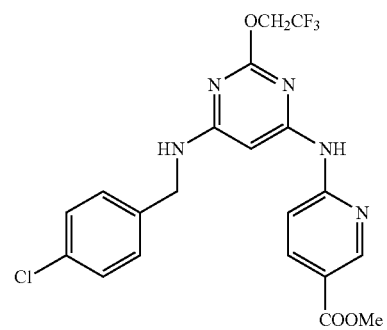

In-1005

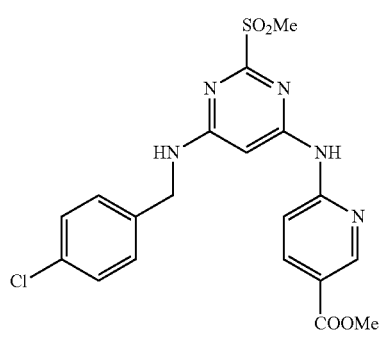

In-1003b 2,2,2-trifluoroethanol (3.88 g) and NaH (1.552 g, 60%) were added into the solution of the mixture of 2-((6-((4-chlorobenzyl)amino)-2-(methylsulfonyl)pyrimidin-4-yl)amino)-5-(methoxycarbonyl)pyridine 1-oxide (In-1003a) and methyl 6-((6-((4-chlorobenzyl)amino)-2-(methylsulfonyl)pyrimidin-4-yl)amino)nicotinate (In-1003b) (1.8 g) in THF (100 mL). The reaction was stirred at room temperature for 72 hours before being quenched by water. The aqueous layer was extracted with EtOAc (3×100 mL). The combined organic phase was dried over $MgSO_4$ and concentrated under vacuum to give a mixture of products, 2-((6-((4-chlorobenzyl)amino)-2-(2,2,2-trifluoroethoxy)pyrimidin-4-yl)amino)-5-(methoxycarbonyl)pyridine 1-oxide (In-1004) and methyl 6-((6-(4-chlorobenzyl)amino)-2-(2,2,2-trifluoroethoxy)pyrimidin-4-yl)amino)nicotinate (In-1005), which was used without purification.

| 2-((6-((4-chlorobenzyl)amino)-2-(2,2,2-trifluoroethoxy)pyrimidin-4-yl)amino)-5-(methoxycarbonyl)pyridine 1-oxide | |
|---|---|
| MS (M + H)+ Calcd. | 484.1 |
| MS (M + H)+ Observ. | 484.5 |
| Retention Time | 1.77 min |
| LC Condition | |
| Solvent A | 5% ACN: 95% Water: 10 mM Ammonium Actetate |
| Solvent B | 95% ACN: 5% Water: 10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN: Water: Ammonium Actetate |
| Column | Phenomenex LUNA C18, 30x2, 3u |

| methyl 6-((6-((4-chlorobenzyl)amino)-2-(2,2,2-trifluoroethoxy)pyrimidin-4-yl)amino)nicotinate | |
|---|---|
| MS (M + H)+ Calcd. | 468.1 |
| MS (M + H)+ Observ. | 468.5 |

| | |
|---|---|
| Retention Time | 1.92 min |
| LC Condition | |
| Solvent A | 5% ACN: 95% Water: 10 mM Ammonium Actetate |
| Solvent B | 95% ACN: 5% Water: 10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN: Water: Ammonium Actetate |
| Column | Phenomenex LUNA C18, 30x2, 3u |

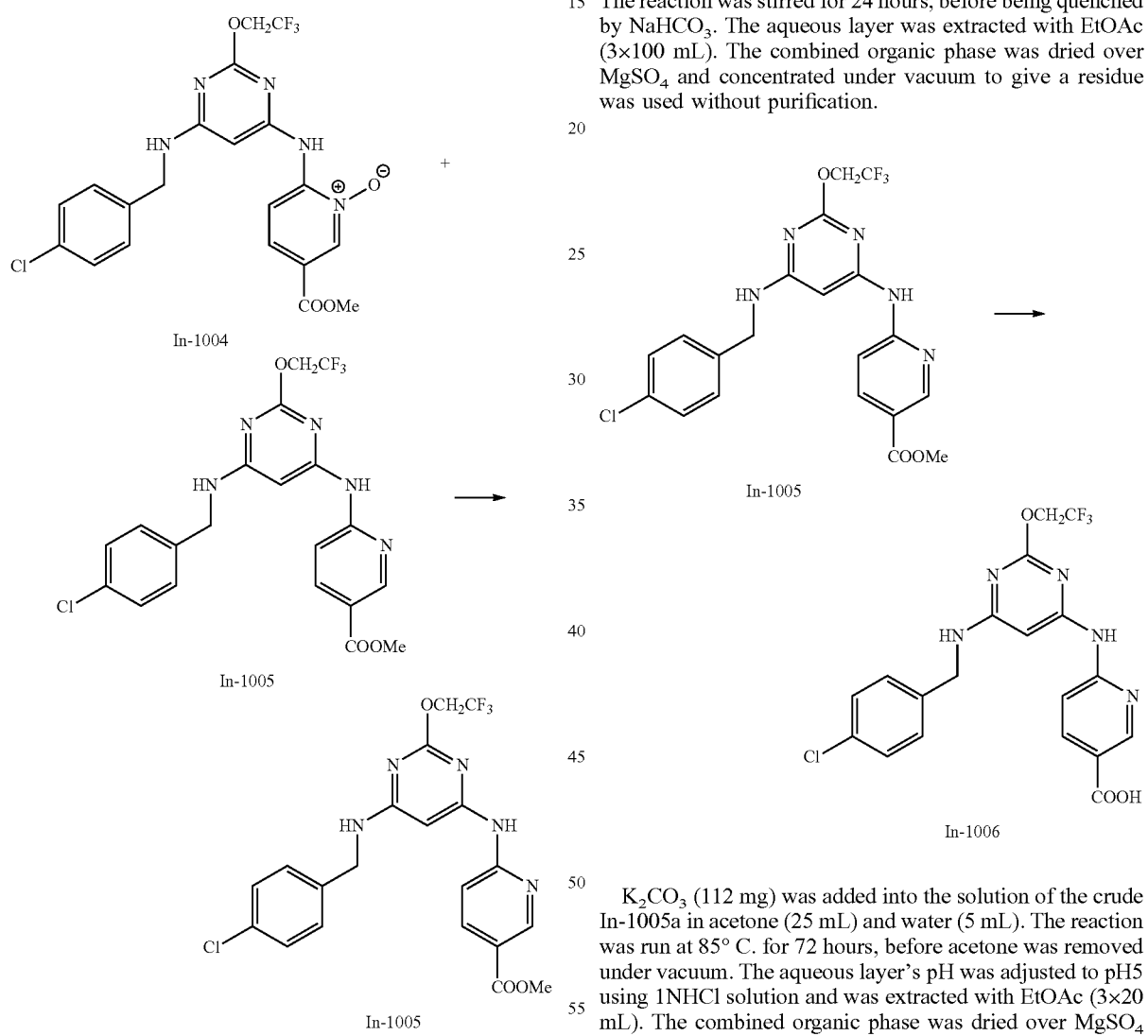

The reaction was stirred for 24 hours, before being quenched by NaHCO₃. The aqueous layer was extracted with EtOAc (3×100 mL). The combined organic phase was dried over MgSO₄ and concentrated under vacuum to give a residue was used without purification.

PCl₃ (483 mg) was added into the solution of the crude mixture of In-1004 and In-1005 (1.7 g) in EtOAc (10 mL).

K₂CO₃ (112 mg) was added into the solution of the crude In-1005a in acetone (25 mL) and water (5 mL). The reaction was run at 85° C. for 72 hours, before acetone was removed under vacuum. The aqueous layer's pH was adjusted to pH5 using 1NHCl solution and was extracted with EtOAc (3×20 mL). The combined organic phase was dried over MgSO₄ and concentrated under vacuum to give the crude 6-((6-((4-chlorobenzyl)amino)-2-(2,2,2-trifluoroethoxy)pyrimidin-4-yl)amino)nicotinic acid (In-1006) which was used without purification.

| 6-((6-((4-chlorobenzyl)amino)-2-(2,2,2-trifluoroethoxy)pyrimidin-4-yl)amino)nicotinic acid | | |
|---|---|---|
| MS (M + H)⁺ Calcd. | | 454.1 |
| MS (M + H)⁺ Observ. | | 454.0 |
| Retention Time | 2.11 min | |

6-((6-((4-chlorobenzyl)amino)-2-(2,2,2-trifluoroethoxy)pyrimidin-4-yl)amino)nicotinic acid

| LC Condition | |
|---|---|
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 2 min |
| Flow Rate | 1 mL/min |
| Wavelength | 220 |
| Solvent Pair | Water-Methanol-TFA |
| Column | PHENOMENEX-LUNA 2.0 × 30 mm 3 um |

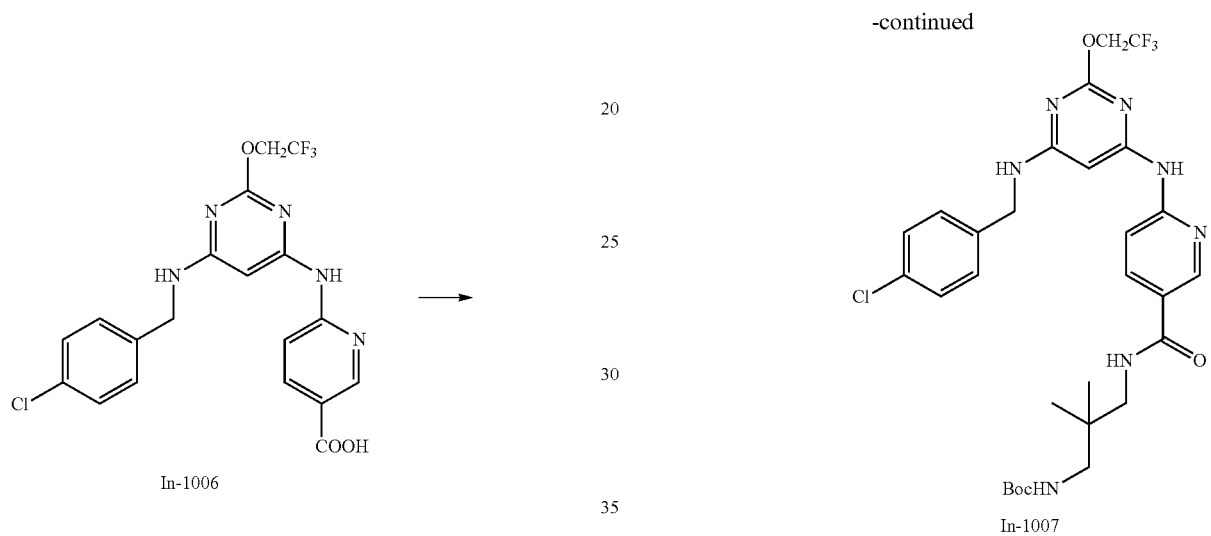

In-1006

In-1007 iPr$_2$NEt (0.5 mL), HCTU (593 mg) were added into the solution of 6-((6-((4-chlorobenzyl)amino)-2-(2,2,2-trifluoroethoxy)pyrimidin-4-yl)amino)nicotinic acid (In-1006) (500 mg) and tert-butyl(3-amino-2,2-dimethylpropyl)carbamate (267 mg) in DMF (20 mL). The reaction was stirred at room temperature for 24 hours before being quenched by NaHCO$_3$. The aqueous layer was extracted with EtOAc (3×20 mL). The combined organic phase was dried over MgSO$_4$ and concentrated under vacuum to give tert-butyl (3-(6-((6-((4-chlorobenzyl)amino)-2-(2,2,2-trifluoroethoxy)pyrimidin-4-yl)amino)nicotinamido)-2,2-dimethylpropyl)carbamate (In-1007) was used without purification.

| tert-butyl (3-(6-((6-((4-chlorobenzypamino)-2-(2,2,2-trifluoroethoxy)pyrimidin-4-yl)amino)nicotinamido)-2,2-dimethylpropyl)carbamate | |
|---|---|
| MS (M + H)$^+$ Calcd. | 638.2 |
| MS (M + H)$^+$ Observ. | 638.2 |
| Retention Time | 2.29 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 2 min |
| Flow Rate | 1 mL/min |
| Wavelength | 220 |
| Solvent Pair | Water-Methanol-TFA |
| Column | PHENOMENEX-LUNA 2.0 × 30 mm 3 um |

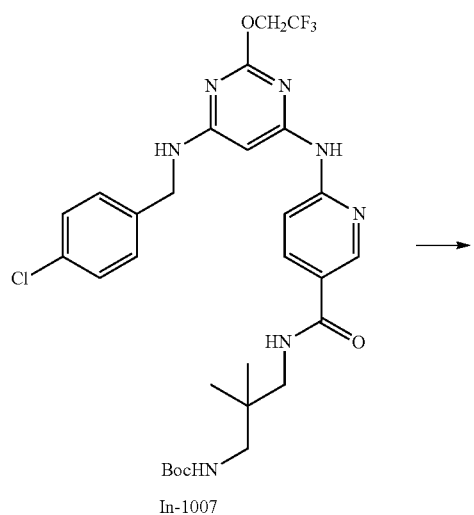

In-1007

→

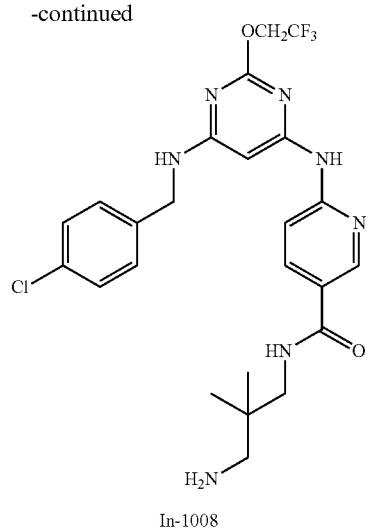

In-1008

TFA (5 mL) was added into a solution of crude tert-butyl (3-(6-((6-((4-chlorobenzyl)amino)-2-(2,2,2-trifluoroethoxy)pyrimidin-4-yl)amino)nicotinamido)-2,2-dimethylpropyl)carbamate (In-1007) (1 g) in CH$_2$CL$_2$ (50 mL). The reaction was carried out at room temperature for 24 hours. After removal of the solvents, the residue was purified by silica gel chromatography to give N-(3-amino-2,2-dimethylpropyl)-6-((6-((4-chlorobenzyl)amino)-2-(2,2,2-trifluoroethoxy)pyrimidin-4-yl)amino)nicotinamide (In-1008).

| N-(3-amino-2,2-dimethylpropyl)-6-((6-((4-chlorobenzyl)amino)-2-(2,2,2-trifluoroethoxy)pyrimidin-4-yl)amino)nicotinamide | |
|---|---|
| MS (M + H)$^+$ Calcd. | 538.2 |
| MS (M + H)$^+$ Observ. | 538.2 |
| Retention Time | 1.91 min |
| | LC Condition |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 2 min |
| Flow Rate | 1 mL/min |
| Wavelength | 220 |
| Solvent Pair | Water-Methanol-TFA |
| Column | PHENOMENEX-LUNA 2.0 × 30 mm 3 um |

General Procedure for the Preparation of Compounds 1001-1019, from In-1008:

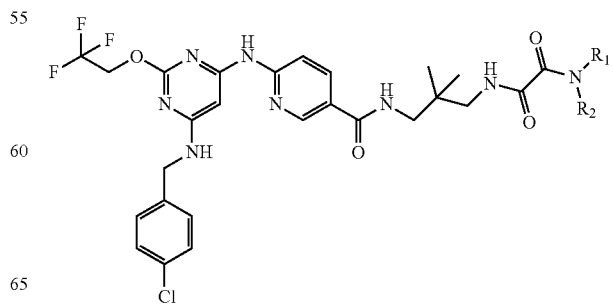

A solution of HATU (201 mg, 532 μmol) in DMF (9.5 mL) was prepared. To each of the carboxylic acids (1 eq.) weighed into 16×48 mm threaded vials was added 500 μL, of the HATU solution. The mixtures were allowed to shake at room temperature for 10 minutes. A solution of N-(3-amino-2,2-dimethylpropyl)-6-((6-((4-chlorobenzyl)amino)-2-(2,2,2-trifluoroethoxy)pyrimidin-4-yl)amino)nicotinamide (In-1008) (190 mg, 1 eq.)) and DIPEA (247 μL) in DMF (9.5 mL) was also prepared. To each of the reaction vials was added 500 μL, of the N-(3-amino-2,2-dimethylpropyl)-6-((6-((4-chlorobenzyl)amino)-2-(2,2,2-trifluoroethoxy)pyrimidin-4-yl)amino)nicotinamide/DIPEA solution. Vials were capped and allowed to shake at room temperature for 18 hours before the mixtures were purified by preparative HPLC systems.

Method M=Column: Waters BEH C18, 2.0×50 mm, 1.7-μm particles; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min.

Method A=Column: Waters BEH C18, 2.0×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min.

| Compd | Structure | MS (M + H)+ Calcd. | MS (M + H)+ Obs. | HPLC Rt (min) | Method |
|---|---|---|---|---|---|
| 1001 | 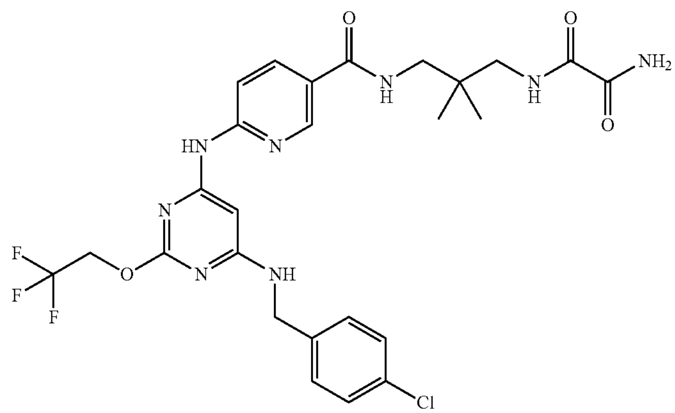 [SMILES: CC(C)(CNC(=O)C(N)=O)CNC(=O)c1ccc(Nc2cc(NCc3ccc(Cl)cc3)nc(OCC(F)(F)F)n2)nc1] | 609.2 | 609.5 | 4.07 | M |
| 1002 | 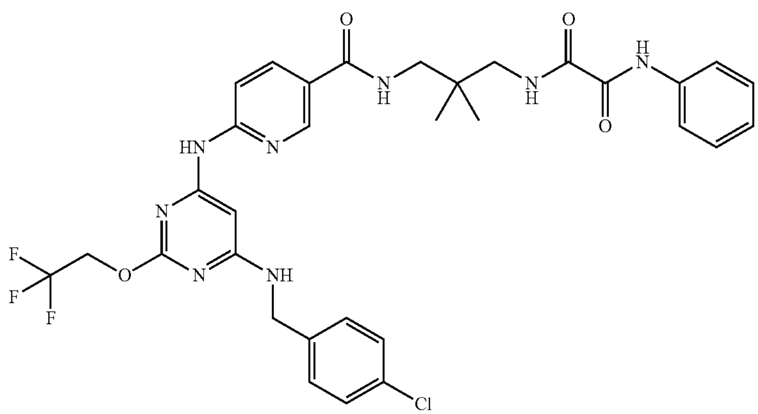 [SMILES: CC(C)(CNC(=O)C(=O)Nc1ccccc1)CNC(=O)c1ccc(Nc2cc(NCc3ccc(Cl)cc3)nc(OCC(F)(F)F)n2)nc1] | 685.2 | 685.6 | 3.36 | A |
| 1003 | 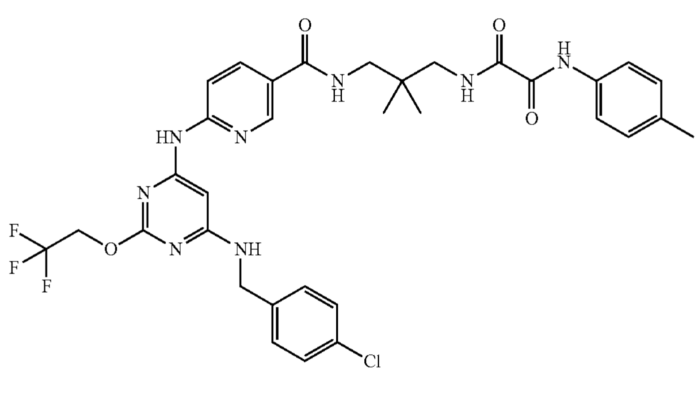 [SMILES: Cc1ccc(NC(=O)C(=O)NCC(C)(C)CNC(=O)c2ccc(Nc3cc(NCc4ccc(Cl)cc4)nc(OCC(F)(F)F)n3)nc2)cc1] | 699.2 | 699.6 | 4.53 | M |

-continued

| Compd | Structure | MS (M + H)+ Calcd. | MS (M + H)+ Obs. | HPLC Rt (min) | Method |
|---|---|---|---|---|---|
| 1004 | 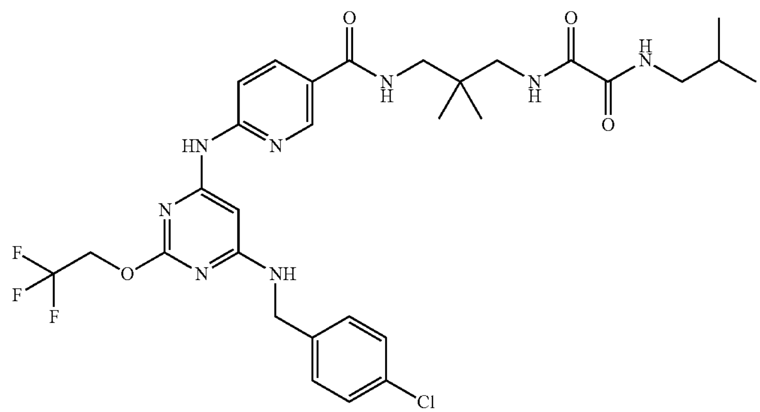 [SMILES: CC(C)CNC(=O)C(=O)NCC(C)(C)CNC(=O)c1ccc(Nc2cc(NCc3ccc(Cl)cc3)nc(OCC(F)(F)F)n2)nc1] | 665.3 | 665.7 | 3.24 | A |
| 1005 | 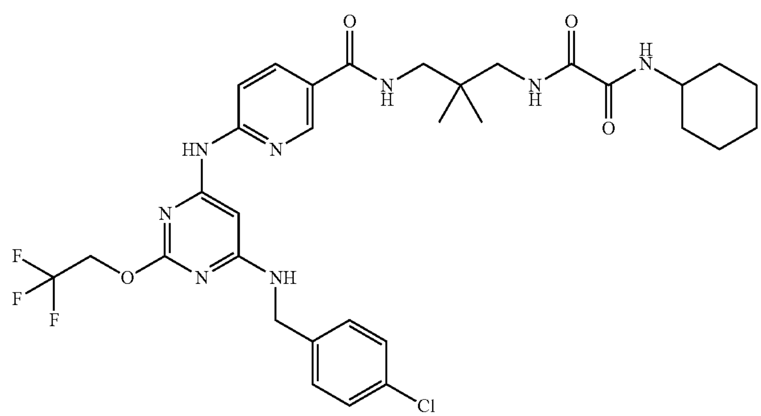 [SMILES: CC(C)(CNC(=O)C(=O)NC1CCCCC1)CNC(=O)c1ccc(Nc2cc(NCc3ccc(Cl)cc3)nc(OCC(F)(F)F)n2)nc1] | 691.3 | 691.8 | 3.39 | A |
| 1006 | 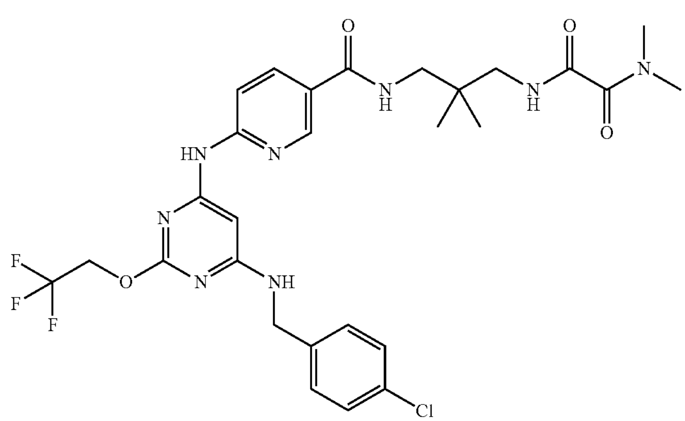 [SMILES: CN(C)C(=O)C(=O)NCC(C)(C)CNC(=O)c1ccc(Nc2cc(NCc3ccc(Cl)cc3)nc(OCC(F)(F)F)n2)nc1] | 637.2 | 637.7 | 4.05 | M |

-continued

| Compd | Structure | MS (M + H)+ Calcd. | MS (M + H)+ Obs. | HPLC Rt (min) | Method |
|---|---|---|---|---|---|
| 1007 | 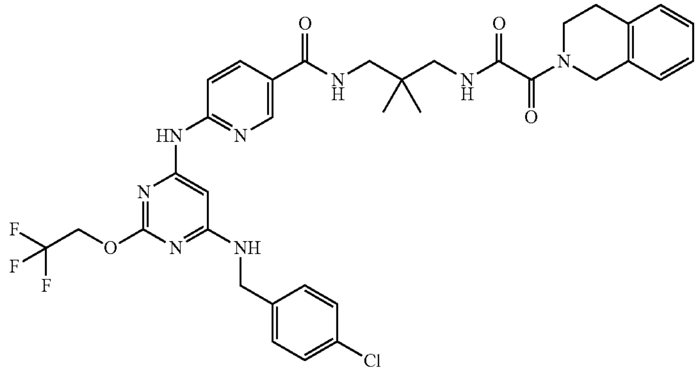 [SMILES: CC(C)(CNC(=O)C(=O)N1CCc2ccccc2C1)CNC(=O)c1ccc(Nc2cc(NCc3ccc(Cl)cc3)nc(OCC(F)(F)F)n2)nc1] | 725.3 | 725.8 | 3.27 | A |
| 1008 | 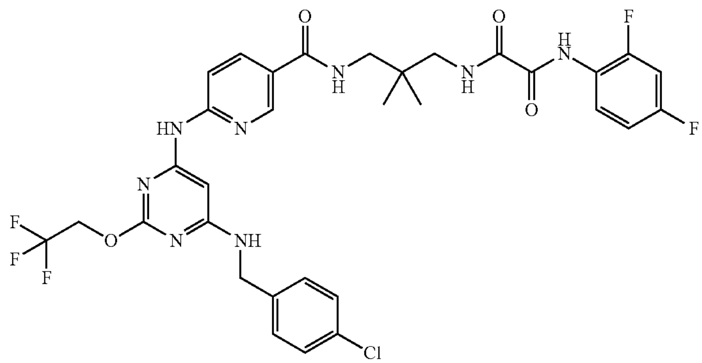 [SMILES: CC(C)(CNC(=O)C(=O)Nc1ccc(F)cc1F)CNC(=O)c1ccc(Nc2cc(NCc3ccc(Cl)cc3)nc(OCC(F)(F)F)n2)nc1] | 721.2 | 721.6 | 4.49 | M |
| 1009 | 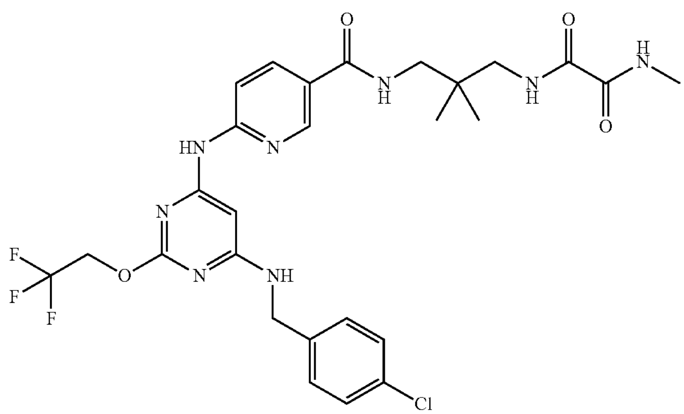 [SMILES: CNC(=O)C(=O)NCC(C)(C)CNC(=O)c1ccc(Nc2cc(NCc3ccc(Cl)cc3)nc(OCC(F)(F)F)n2)nc1] | 623.2 | 623.5 | 4.14 | M |
| 1010 | 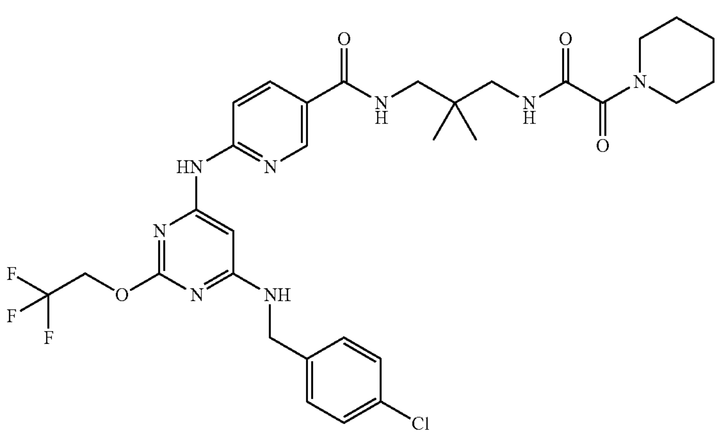 [SMILES: CC(C)(CNC(=O)C(=O)N1CCCCC1)CNC(=O)c1ccc(Nc2cc(NCc3ccc(Cl)cc3)nc(OCC(F)(F)F)n2)nc1] | 677.3 | 677.8 | 3.07 | A |

-continued

| Compd | Structure | MS (M + H)+ Calcd. | MS (M + H)+ Obs. | HPLC Rt (min) | Method |
|---|---|---|---|---|---|
| 1011 | 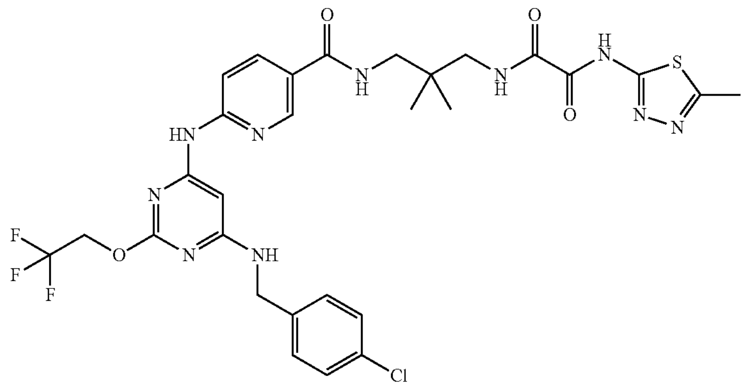 [SMILES: Cc1nnc(NC(=O)C(=O)NCC(C)(C)CNC(=O)c2ccc(Nc3cc(NCc4ccc(Cl)cc4)nc(OCC(F)(F)F)n3)nc2)s1] | 707.2 | 707.5 | 4.18 | M |
| 1012 | 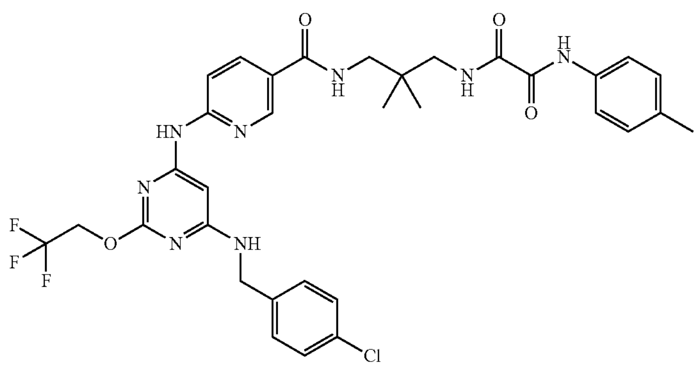 [SMILES: Cc1ccc(NC(=O)C(=O)NCC(C)(C)CNC(=O)c2ccc(Nc3cc(NCc4ccc(Cl)cc4)nc(OCC(F)(F)F)n3)nc2)cc1] | 703.2 | 703.5 | 3.37 | A |
| 1013 | 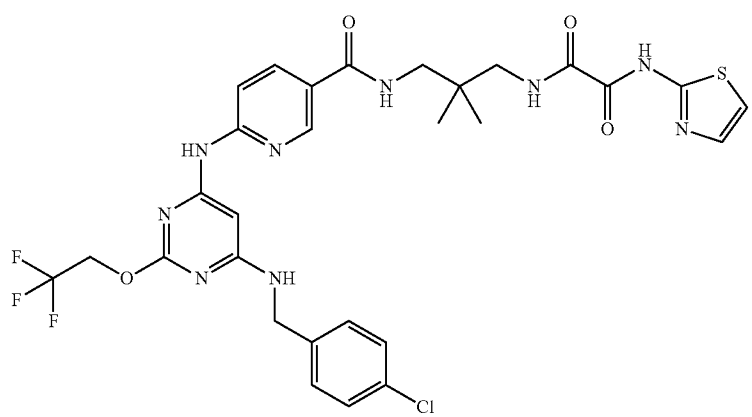 [SMILES: CC(C)(CNC(=O)C(=O)Nc1nccs1)CNC(=O)c1ccc(Nc2cc(NCc3ccc(Cl)cc3)nc(OCC(F)(F)F)n2)nc1] | 692.2 | 692.5 | 4.31 | M |
| 1014 | 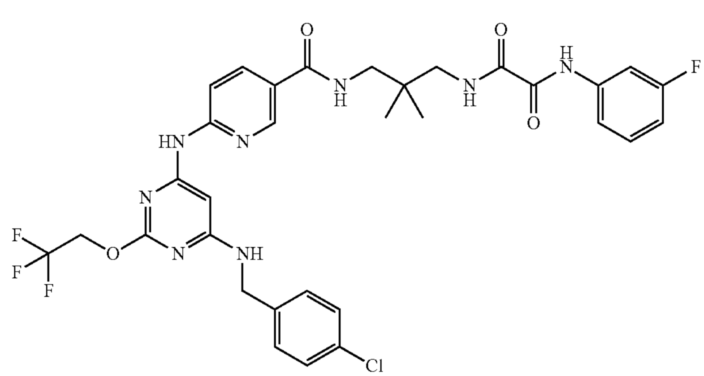 [SMILES: CC(C)(CNC(=O)C(=O)Nc1cccc(F)c1)CNC(=O)c1ccc(Nc2cc(NCc3ccc(Cl)cc3)nc(OCC(F)(F)F)n2)nc1] | 703.2 | 703.6 | 4.47 | M |

| Compd | Structure | MS (M + H)+ Calcd. | MS (M + H)+ Obs. | HPLC Rt (min) | Method |
|---|---|---|---|---|---|
| 1015 | 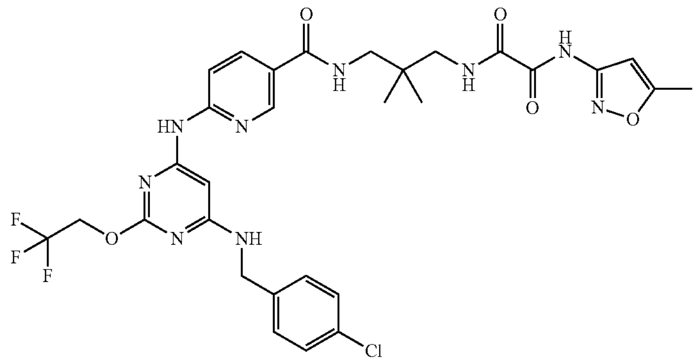 [SMILES: Cc1cc(NC(=O)C(=O)NCC(C)(C)CNC(=O)c2ccc(Nc3cc(NCc4ccc(Cl)cc4)nc(OCC(F)(F)F)n3)nc2)no1] | 690.2 | 690.7 | 4.22 | M |
| 1016 | 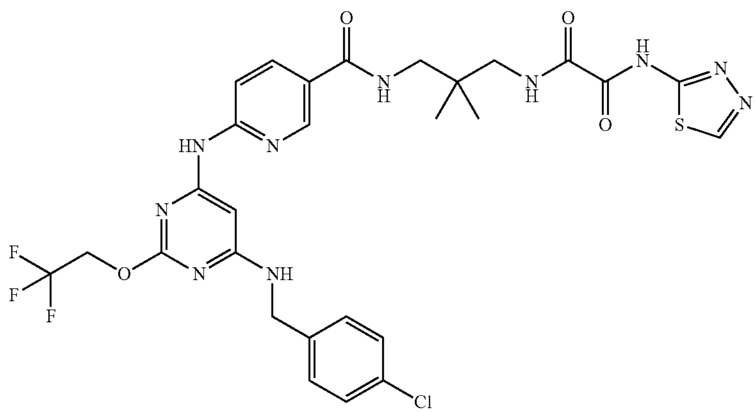 [SMILES: CC(C)(CNC(=O)C(=O)Nc1nncs1)CNC(=O)c1ccc(Nc2cc(NCc3ccc(Cl)cc3)nc(OCC(F)(F)F)n2)nc1] | 693.2 | 693.7 | 4.01 | M |
| 1017 | 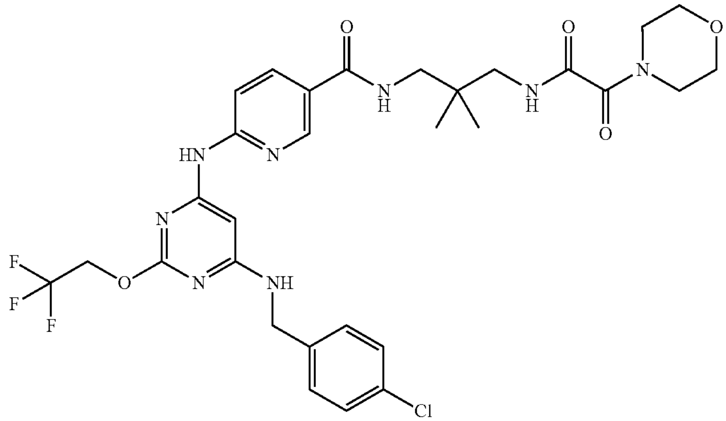 [SMILES: CC(C)(CNC(=O)C(=O)N1CCOCC1)CNC(=O)c1ccc(Nc2cc(NCc3ccc(Cl)cc3)nc(OCC(F)(F)F)n2)nc1] | 679.2 | 678.8 | 4.05 | M |
| 1018 | 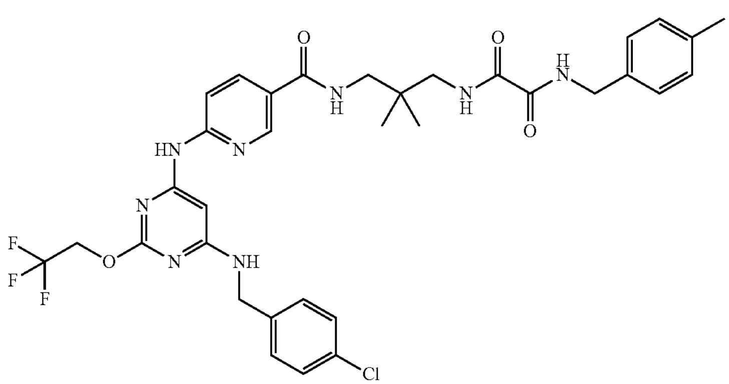 [SMILES: Cc1ccc(CNC(=O)C(=O)NCC(C)(C)CNC(=O)c2ccc(Nc3cc(NCc4ccc(Cl)cc4)nc(OCC(F)(F)F)n3)nc2)cc1] | 717.2 | 717.6 | 4.33 | M |

| Compd | Structure | MS (M + H)+ Calcd. | MS (M + H)+ Obs. | HPLC Rt (min) | Method |
|---|---|---|---|---|---|
| 1019 | 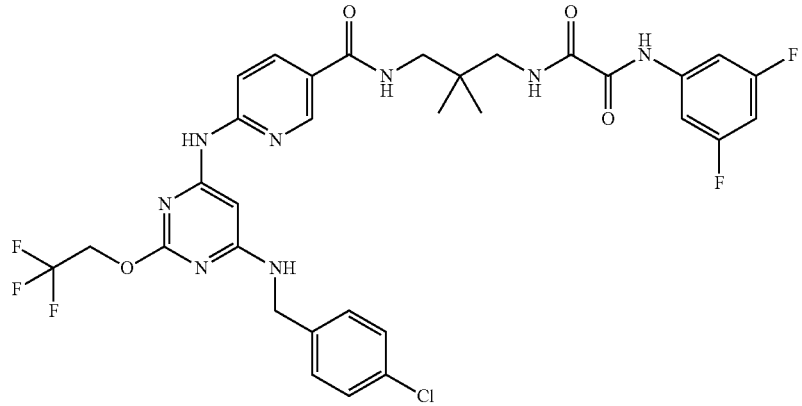 [SMILES: CC(C)(CNC(=O)C(=O)Nc1cc(F)cc(F)c1)CNC(=O)c1ccc(Nc2cc(NCc3ccc(Cl)cc3)nc(OCC(F)(F)F)n2)nc1] | 721.2 | 721.7 | 4.48 | M |

Preparation of Compounds 1020:

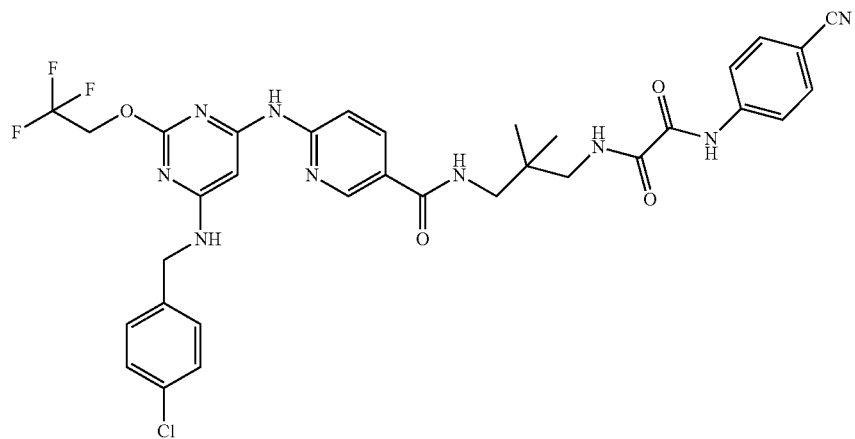 [SMILES: CC(C)(CNC(=O)C(=O)Nc1ccc(C#N)cc1)CNC(=O)c1ccc(Nc2cc(NCc3ccc(Cl)cc3)nc(OCC(F)(F)F)n2)nc1]

iPr$_2$NEt (0.5 mL), HATU (182 mg) were added into the solution of 6-((6-((4-chlorobenzyl)amino)-2-(2,2,2-trifluoroethoxy)pyrimidin-4-yl)amino)nicotinic acid (200 mg) and N$_1$-(3-amino-2,2-dimethylpropyl)-N$_2$-(4-cyanophenyl)oxalamide hydrochloride (137 mg) in THF (20 mL). The reaction was stirred at room temperature for 24 hours. The solvents were removed under vacuum and the residue was purified by preparative HPLC system.

| Compound 1020 | |
|---|---|
| MS (M + H)+ Calcd. | 710.2 |
| MS (M + H)+ Observ. | 710.2 |
| Retention Time | 2.24 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 2 min |
| Flow Rate | 1 mL/min |
| Wavelength | 220 |
| Solvent Pair | Water-Methanol-TFA |
| Column | PHENOMENEX-LUNA 2.0 × 30 mm 3 um |

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:
1. A compound of formula I

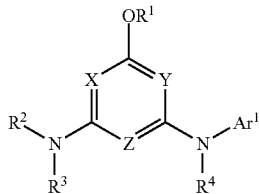

where
X and Y are N and Z is CH; Y and Z are N and X is CH; or X and Z are N and Y is CH;
R$^1$ is alkyl, hydroxyalkyl, alkoxyalkyl, haloalkyl, cycloalkyl, hydroxycycloalkyl, alkoxycycloalkyl, halocycloalkyl, cycloalkenyl, indanyl, alkylcarbonyl, or benzyl wherein the benzyl moiety is substituted with 0-3 substituents selected from halo, alkyl, haloalkyl, alkoxy, and haloalkoxy;
R$^2$ is alkyl, (Ar$^2$)alkyl, (Ar$^2$)cycloalkyl, ((Ar$^2$)cycloalkyl)alkyl, ((Ar$^2$)alkyl)cycloalkyl, or (((Ar$^2$)alkyl)cycloalkyl)alkyl;
R$^3$ is hydrogen or alkyl;
R$^4$ is hydrogen or alkyl;
R$^5$ is

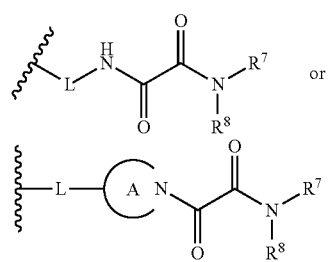

where ring A is a 4 to 7 membered alkylene ring substituted with L;
R$^6$ is hydrogen or alkyl;
R$^7$ is hydrogen, alkyl, cycloalkyl, (cycloalkyl)alkyl, (alkyl)cycloalkyl, ((alkyl))cycloalkyl)alkyl, a bridged bicycloalkyl, or Ar$^3$, and is substituted with 0-4 substituents selected from the group consisting of halo, alkyl, cycloalkyl, hydroxyalkyl, alkoxyalkyl, hydroxy, alkoxy, benzyloxy, CO$_2$R$^9$, N(R$^{10}$)(R$^{11}$), tetrahydrofuranyl, tetrahydropyranyl, and Ar$^4$;
R$^8$ is hydrogen or alkyl;
or R$^7$ and R$^8$ taken together with the nitrogen to which they are attached is azetidinyl, pyrrolidinyl, piperidinyl, piperazinyl, morpholinyl, or tetrahydroisoquinolinyl, and is substituted with 0-2 substituents selected from alkyl, alkylcarbonyl, and alkoxycarbonyl;
R$^9$ is hydrogen, alkyl, hydroxyalkyl, alkoxyalkyl, ((hydroxyalkyl)alkoxy)alkoxy, or ((alkoxy)alkoxy)alkoxy;
R$^{10}$ is hydrogen, alkyl, cycloalkyl, alkylcarbonyl, or alkoxycarbonyl;
R$^{11}$ is hydrogen or alkyl;
or R$^{10}$ and R$^{11}$ taken together with the nitrogen to which they are attached is azetidinyl, pyrrolidinyl, piperidinyl, piperazinyl, or morpholinyl, and is substituted with 0-2 substituents selected from alkyl, alkylcarbonyl, and alkoxycarbonyl;

R$^{12}$ is hydrogen or alkyl;
R$^{13}$ is hydrogen, alkyl, cycloalkyl, alkylcarbonyl, or alkoxycarbonyl;
R$^{14}$ is hydrogen or alkyl;
or R$^{13}$ and R$^{14}$ taken together with the nitrogen to which they are attached is azetidinyl, pyrrolidinyl, piperidinyl, piperazinyl, or morpholinyl, and is substituted with 0-2 substituents selected from alkyl, alkylcarbonyl, and alkoxycarbonyl;
L is alkylene, cycloalkylene, (cycloalkyl)alkyl, (alkyl)cycloalkyl, or alkyl(cycloalkyl)alkyl, and is substituted with 0-2 substituents selected from alkoxy, hydroxy, CO$_2$R$^{12}$ and CONR$^{13}$R$^{14}$;
Ar$^1$ is phenyl, pyridinyl or pyrimidinyl, and is substituted with 1 CON(R$^5$)(R$^6$) and with 0-3 substituents selected from halo, alkyl, haloalkyl, alkoxy, and haloalkoxy;
Ar$^2$ is phenyl substituted with 0-3 substituents selected from halo, alkyl, haloalkyl, alkoxy, and haloalkoxy;
Ar$^3$ is phenyl, indanyl, fluorenyl, biphenyl, terphenyl, pyridinyl, pyrazolyl, isoxazolyl, isothiazolyl, imidazolyl, oxazolyl, thiazolyl, triazolyl, oxadiazolyl, thiadiazolyl, benzoxazolyl, indolinyl, or dibenzofuranyl, and is substituted with 0-3 substituents selected from cyano, halo, alkyl, alkenyl, haloalkyl, cycloalkyl, (CO$_2$R$^{12}$)alkyl, (CO$_2$R$^{12}$)alkenyl, (CON(R$^{13}$)(R$^{14}$))alkyl, phenyl, hydroxyl, alkoxy, haloalkoxy, alkylcarbonyl, CO$_2$R$^{12}$, and CON(R$^{13}$)(R$^{14}$);
or Ar$^3$ is phenyl substituted with 1 substituent selected from benzyl, tetrazolyloxy, thiazolyl, phenylpyrazolyl, methyloxadiazolyl, thiadiazolyl, triazolyl, methyltriazolyl, tetrazolyl, pyridinyl, and dimethoxypyrimdinyl; and
Ar$^4$ is phenyl, indanyl, tetrahydronaphthyl, isochromanyl, benzodioxolyl, pyridinyl, pyrazolyl, imidazolyl, or triazolyl and is substituted with 0-3 substituents selected from cyano, halo, alkyl, alkyenyl, haloalkyl, alkoxy, and haloalkoxy, N(R$^{13}$)(R$^{14}$), and alkylCO;
or a pharmaceutically acceptable salt thereof.

2. A compound of claim 1 where
X and Y are N and Z is CH;
R$^1$ is haloalkyl;
R$^2$ is (Ar$^2$)alkyl;
R$^3$ is hydrogen;
R$^4$ is hydrogen;
R$^5$ is

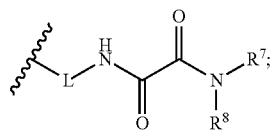

R$^6$ is hydrogen or alkyl;
R$^7$ is hydrogen, alkyl, cycloalkyl, or Ar$^3$;
R$^8$ is hydrogen or alkyl;
or R$^7$ and R$^8$ taken together with the nitrogen to which they are attached is piperidinyl, morpholinyl, or tetrahydroisoquinolinyl;
L is alkylene;
Ar$^1$ is pyridinyl substituted with 1 CON(R$^5$)(R$^6$);
Ar$^2$ is phenyl substituted with 0-3 halo substituents; and
Ar$^3$ is phenyl, isoxazolyl, thiazolyl, or thiadiazolyl, and is substituted with 0-3 substituents selected from cyano, halo, alkyl, haloalkyl, alkoxy, and haloalkoxy;
or a pharmaceutically acceptable salt thereof.

3. A compound of claim 1 where $R^1$ is haloalkyl; $R^2$ is $(Ar^2)$alkyl; $R^3$ is hydrogen; $R^4$ is hydrogen; $R^7$ is hydrogen, alkyl, cycloalkyl, or $Ar^3$; L is

$Ar^1$ is phenyl substituted with 1 $CON(R^5)(R^6)$; $Ar^2$ is phenyl substituted with 1 halo; and $Ar^3$ is phenyl, isoxazolyl, thiazolyl, or thiadiazolyl, and is substituted with 0-1 substituents selected from cyano, halo, and alkyl; or a pharmaceutically acceptable salt thereof.

4. A compound of claim 1 where $R^1$ is haloalkyl or a pharmaceutically acceptable salt thereof.

5. A compound of claim 1 where $R^1$ is trifluroethyl or a pharmaceutically acceptable salt thereof.

6. A compound of claim 1 where $R^2$ is $(Ar^2)$alkyl or $(Ar^2)$cycloalkyl, or a pharmaceutically acceptable salt thereof.

7. A compound of claim 1 where $R^3$ is hydrogen and $R^4$ is hydrogen, or a pharmaceutically acceptable salt thereof.

8. A compound of claim 1 where $R^7$ is hydrogen, alkyl, cycloalkyl, or $Ar^3$; $R^8$ is hydrogen or alkyl; or $R^7$ and $R^8$ taken together with the nitrogen to which they are attached is piperidinyl, morpholinyl, or tetrahydroisoquinolinyl; or a pharmaceutically acceptable salt thereof.

9. A compound of claim 1 where $R^7$ is $Ar^3$ or a pharmaceutically acceptable salt thereof.

10. A compound of claim 1 where L is

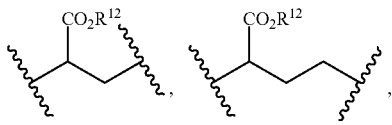

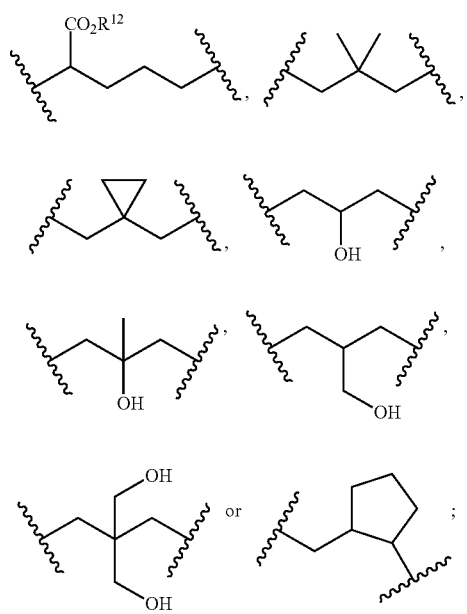

or a pharmaceutically acceptable salt thereof.

11. A compound of claim 1 where $Ar^1$ is pyridinyl substituted with 1 $CON(R^5)(R^6)$, or a pharmaceutically acceptable salt thereof.

12. A composition comprising a compound of claim 1, or a pharmaceutically acceptable salt thereof, and a pharmaceutically acceptable carrier.

13. A method of treating hepatitis C infection comprising administering a therapeutically effective amount of a compound of claim 1 to a patient.

* * * * *

UNITED STATES PATENT AND TRADEMARK OFFICE
CERTIFICATE OF CORRECTION

PATENT NO. : 9,656,992 B2
APPLICATION NO. : 14/771914
DATED : May 23, 2017
INVENTOR(S) : Wang et al.

Page 1 of 1

It is certified that error appears in the above-identified patent and that said Letters Patent is hereby corrected as shown below:

In the Claims

Claim 1, Column 57, Line 46:
Delete "((alkyl))cycloalkyl)alkyl," and insert -- ((alkyl)cycloalkyl)alkyl, --.

Claim 1, Column 58, Line 32:
Delete "dimethoxypyrimdinyl;" and insert -- dimethoxypyrimidinyl; --.

Claim 5, Column 59, Line 17:
Delete "$R^{1"}$" and insert -- $R^1$ --.

Claim 11, Column 60, Line 29:
Delete "$CON(R^5)(R^6)$ ," and insert -- $CON(R^5)(R^6)$, --.

Signed and Sealed this
Twenty-first Day of May, 2019

Andrei Iancu
*Director of the United States Patent and Trademark Office*